с

US005985553A

United States Patent [19]
King et al.

[11] Patent Number: 5,985,553
[45] Date of Patent: Nov. 16, 1999

[54] ERBB-2 GENE SEGMENTS, PROBES, RECOMBINANT DNA AND KITS FOR DETECTION

[75] Inventors: C. Richter King, Washington, D.C.; Matthias H. Kraus, Bethesda, Md.; Stuart A. Aaronson, Great Falls, Va.

[73] Assignee: The United States of America as represented by the Department of Health and Human Services, Washington, D.C.

[21] Appl. No.: 08/475,035

[22] Filed: Jun. 7, 1995

Related U.S. Application Data

[62] Division of application No. 07/786,598, Nov. 1, 1991, Pat. No. 5,747,261, which is a division of application No. 07/110,791, Oct. 21, 1987, which is a continuation-in-part of application No. 06/836,414, Mar. 5, 1986, abandoned.

[51] Int. Cl.$^6$ ...................................................... C12Q 1/68
[52] U.S. Cl. ......................... 435/6; 435/69.1; 435/172.3; 435/320.1; 435/810; 436/501; 436/63; 536/23.1; 536/24.1; 536/24.3; 536/24.31; 536/24.32; 536/24.33; 935/77; 935/78
[58] Field of Search ........................... 435/6, 69.1, 172.3, 435/320.1, 810; 436/501, 63; 536/23.1, 24.1, 24.3–33; 935/77, 78

[56] References Cited

U.S. PATENT DOCUMENTS

| 4,753,894 | 6/1988 | Frankel et al. ........................... 436/548 |
| 4,968,603 | 11/1990 | Slamon et al. ............................... 435/6 |

FOREIGN PATENT DOCUMENTS

WO 93/16185  8/1993  WIPO .

OTHER PUBLICATIONS

New England Biolabs Catalog (Published By New England Biolabs, Beverly, MA, USA 1986/87) pp. 60–62.
A.A. King, et al. Cell Membr. Cancer Proc. Intl. Workshop, 2nd., pp. 411–416 (1985).

BB. Semba, et al. "A v–*erbB*–related protooncogene, c–*erbB*–2, is distinct from the c–*erbB*–1/epidermal growth factor–receptor gene and is amplified in a human salivary gland adenocarcinoma" PNAS, USA 82: 6497–6501 (Oct., 1985).

CC. Schechter, et al. "The *neu* oncogene: an *erb*–*B*–related gene encoding a 185,000–$M_r$ tumour antigen" Nature 312: 513–516 (Dec. 6, 1984).

DD. King, et al. "Amplification of a Novel erbB–Related Gene in a Human Mammary Carcinoma" Science 229: 974–6 (Sep. 6, 1985).

EE. Schecter, et al. Science 229: 976–8 (Sep. 6, 1985).

FF. King, et al. "Oncogenes as growth factors . . . erbB–related gene" in Chem. Abstracts 104(17): 142890e (Apr. 28, 1986) (corresponds to AA).

Palk, S. et al. "Pathologic Findings From the National Surgical Adjuvant Breast and Bowel Project; Prognostic Significence of erbB–2 Protein Overexpression in Primary Breast Cancer" *J. of Clinical Oncology* (1990) 5:103–112.

King, C.B. et al. "Hetergeneous Expression of erbB–2 Messenger RNA in Human Breast Cancer" Cancer Research(1989) 49:4185–4191.

Park, J–S, et al, "Application, Overexpression, and Rearrangement of erbB–2 Protooncogene in Primary Human Stomach Carcinomes" Cancer Research (1989) 49:6605–6609.

(List continued on next page.)

*Primary Examiner*—Ardin H. Marschel
*Attorney, Agent, or Firm*—Needle & Rosenberg, P.C.

[57] ABSTRACT

The isolation, cloning and characterization of a human gene related to but distinct from the EGF receptor gene has been described. Nucleotide sequence of the gene and amino acid sequence of the polypeptide encoded by the gene have been determined. The use of the nucleic acid probes and antibodies having specific binding affinity with said polypeptide for diagnostic and therapeutic purposes has also been described.

22 Claims, 12 Drawing Sheets

OTHER PUBLICATIONS

King, C.R. et al. "Implications of erbB–2 overexpression for basic science and clinical medicine" Examiners in Cancer Biology (1990) 1:329–337.

Berger, M.S. et al. "Correlation of c–erbB–2 Gene Amplification and Protein Expression in Human Breast Carcinoma with Model Status and Nuclear Grading" Cancer Research (1988) 48:1238–1243.

A. Ullrich et al., "Human epidermal growth factor receptor cDNA sequence and aberrant expression of the amplified gene A431 epidermoid carcinoma cells," Nature (1984) vol. 309, pp. 418–425.

King et al., Amplification of a Novel v–erbB–Related Gene in a Human Mammary Carcinoma, *Science,* (1985) 229:974–976.

Kraus et al., Overexpression of the EGF Receptor–Related Proto–Oncogene erbB–2 in Human Mammary Tumor Cell Lines . . . *The EMBO Journal,* (1987) 6:605–610.

Di Foire et al., erbB–2 Is A Potent Oncogene When Overexpressed in NIH/3T3 Cells, *Science.,* , (1987) 237:178–182.

Lacroix et al., Overexpression of erbB–2 or EGF Receptor Proteins Present In Early Stage Mammary . . . Oncogene, (1989) 4:145–151.

Slamon et al., Human Breast Cancer: Correlation of Relapse and Survival with . . . , *Science,* (1987), 235:177–182.

Downward, et al. *Nature* 307:521–527, 1984.

Ullrich, et al., *Nature* 309:418–425, 1984.

Doolittle, et al. *Science* 221:275–277, 1983.

Lin, et al. *Science* 224:843, 1984.

Rigby, et al., *J. Mol. Biol.* 113:237, 1977.

Wahl, et al. *Proc. Natl. Acad. Sci USA* 76:3686, 1979.

de Klein, et al., *Nature* 300:765, 1982.

Collins, et al. *Proc. Natl. Acad. Sci. USA* 80:4813, 1983.

Liberman, et al., *Nature* 313:144, 1985.

Kasuga et al. *Nature* 298:667–669, 1982.

Rubin, et al. *Nature* 305:438–440, 1983.

Yamamoto, et al. *Cell* 35:71–78, 1983.

Land et al., *Science* 222:771–778, 1983.

Cohen, et al., *J. Biol. Chem* 255:4834–4842, 1980.

Nishimura, et al. *Proc. Natl. Acad. Sci. USA* 79:4303–4307, 1982.

Sedlak (1994) Genetic Engineering News of May 15, 1994, pp. 8–9.

Brison (1993) *Biochemica et Biophysica Acta,* vol. 1155, pp. 25–41.

Sembo et al. (1985) *Proc. Natl. Acad. Sci.* (USA), vol. 82, pp. 6497–6501.

Yamamoto et al. (1986) *Nature,* vol. 319, pp. 230–234.

Ring et al. "Identity of BCA200 and c–erbB–2 Indicated by Reactivity of Monoclonal Antibodies with Recombinant c–erbB–2" *Mol. Immunol.* 28(8):915–917, 1991.

Ring et al. "Distribution and Physical Properties of BCA200, a M, 200,000 Glycoprotein Selectively Associated with Human Breast Cancer" *Cancer Res.* 49:3070–3080, Jun. 1, 1989.

Coussens et al. "Tyrosine Kinase Receptor with Extensive Homology to EGF Receptor Shares Chromosomal Location with neu Oncogene" *Science* 230:1132–1139, Dec. 6, 1985.

Pirker et al. "Characterization of Immunotoxins Active Against Ovarian Cancer Cell Lines" *J. Clin. Invest.* 76:1261–1267, Sep. 1985.

Frankel et al. "Tissue Distribution of Breast Cancer–Associated Antigens Defined by Monoclonal Antibodies" *J. Biol. Resp. Modifiers* 4:273–286, 1985.

Bjorn et al. "Evaluation of Monoclonal Antibodies for the Development of Breast Cancer Immunotoxins" *Cancer Res.* 45:1214–1221, Mar. 1985.

FIG. 3

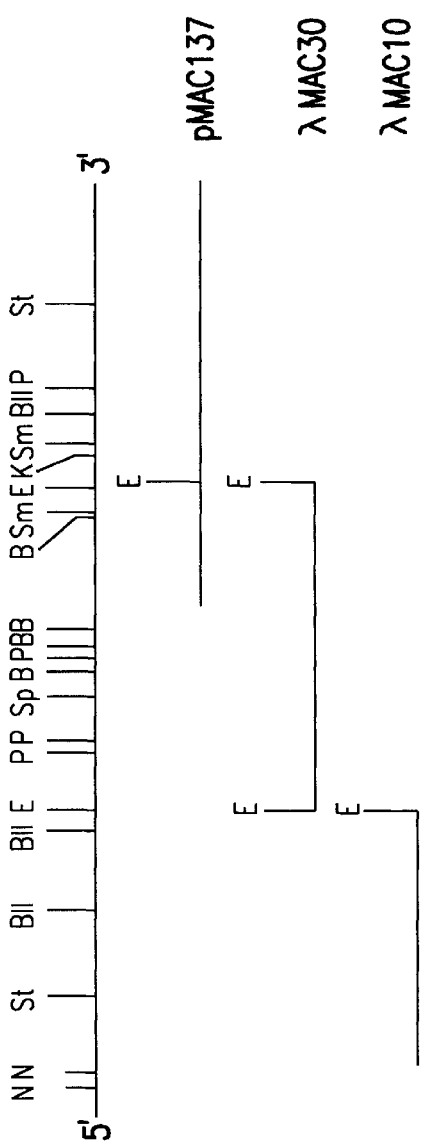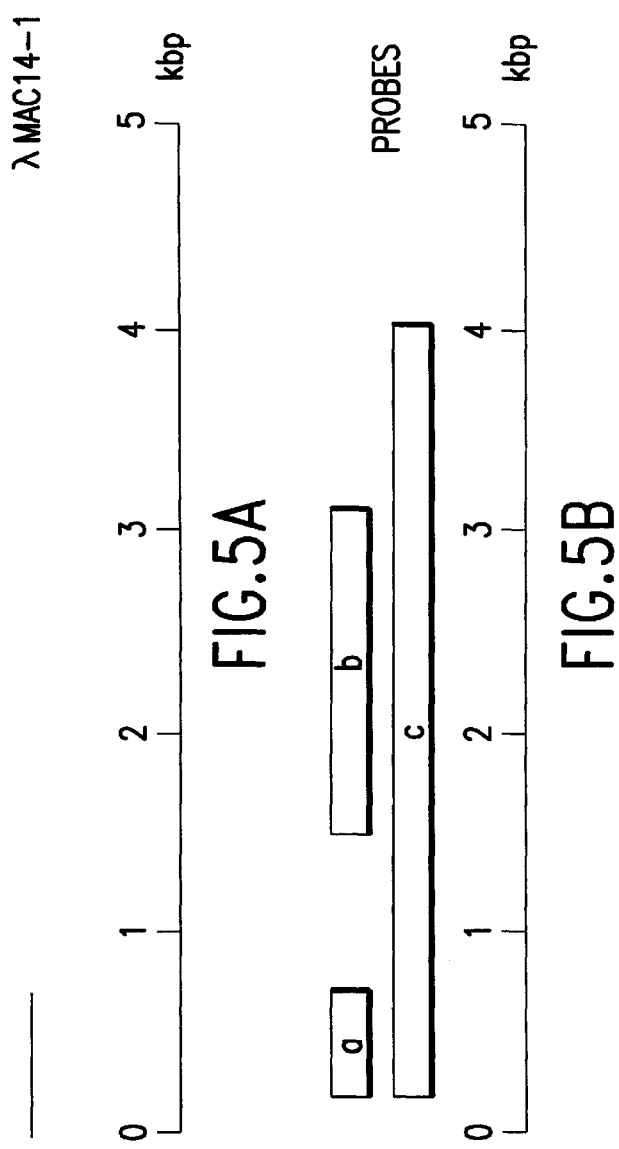
FIG.5A
FIG.5B

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 78 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Gly Met Ser Tyr Leu Glu Asp Val Arg Leu Val His Arg Asp Leu Ala
 1               5                  10                  15

Ala Arg Asn Val Leu Val Lys Ser Pro Asn His Val Lys Ile Thr Asp
                20                  25                  30

Phe Gly Leu Ala Arg Leu Leu Asp Ile Asp Glu Thr Glu Tyr His Ala
            35                  40                  45

Asp Gly Gly Lys Val Pro Ile Lys Trp Met Ala Leu Glu Ser Ile Leu
        50                  55                  60

Arg Arg Arg Phe Thr His Gln Ser Asp Val Trp Ser Tyr Gly
65                  70                  75
```

(2) INFORMATION FOR SEQ ID NO:2:

(i) SEQUENCE CHARACTERISTICS:
      (A) LENGTH: 424 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
GTCTACATGG GTGCTTCCCA TTCCAGGGGA TGAGCTACCT GGAGGATGTG CGGCTCGTAC    60

ACAGGGACTT GGCCGCTCGG AACGTGCTGG TCAAGAGTCC CAACCATGTC AAAATTACAG   120

ACTTCGGGCT GGCTCGGCTG CTGGACATTG ACGAGACAGA GTACCATGCA GATGGGGCA    180

AGGTTAGGTG AAGGACCAAG GAGCAGAGGA GGCTGGGTGG AGTGGTGTCT AGCCCATGGG   240

AGAACTCTGA GTGGCCACCT CCCCACAACA CACAGTTGGA GGACTTCCTC TTCTGCCCTC   300

CCAGGTGCCC ATCAAGTGGA TGGCGCTGGA GTCCATTCTC CGCCGGCGGT TCACCCACCA   360

GAGTGATGTG TGGAGTTATG GTGTGTGATG GGGGTGTTG GGAGGGGTGG GTGAGGAGCC    420

ATGG                                                                424
```

(2) INFORMATION FOR SEQ ID NO:3:

(i) SEQUENCE CHARACTERISTICS:
        (A) LENGTH: 5532 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 187..3816

(xi) SEQUENCE DESCRIPTION: SEQ ID NO:3:

```
GCCGCGCTGC GCCGGAGTCC CGAGCTAGCC CCGGCGCCGC CGCCGCCCAG ACCGGACGAC    60

AGGCCACCTC GTCGGCGTCC GCCCGAGTCC CCGCCTCGCC GCCAACGCCA CAACCACCGC   120

GCACGGCCCC CTGACTCCGT CCAGTATTGA TCGGGAGAGC CGGAGCGAGC TCTTCGGGGA   180

GCAGCG ATG CGA CCC TCC GGG ACG GCC GGG GCA GCG CTC CTG GCG CTG    228
       Met Arg Pro Ser Gly Thr Ala Gly Ala Ala Leu Leu Ala Leu
         1               5                  10

CTG GCT GCG CTC TGC CCG GCG AGT CGG GCT CTG GAG GAA AAG AAA GTT    276
Leu Ala Ala Leu Cys Pro Ala Ser Arg Ala Leu Glu Glu Lys Lys Val
 15                  20                  25                  30

TGC CAA GGC ACG AGT AAC AAG CTC ACG CAG TTG GGC ACT TTT GAA GAT    324
Cys Gln Gly Thr Ser Asn Lys Leu Thr Gln Leu Gly Thr Phe Glu Asp
                 35                  40                  45

CAT TTT CTC AGC CTC CAG AGG ATG TTC AAT AAC TGT GAG GTG GTC CTT    372
His Phe Leu Ser Leu Gln Arg Met Phe Asn Asn Cys Glu Val Val Leu
             50                  55                  60

GGG AAT TTG GAA ATT ACC TAT GTG CAG AGG AAT TAT GAT CTT TCC TTC    420
Gly Asn Leu Glu Ile Thr Tyr Val Gln Arg Asn Tyr Asp Leu Ser Phe
         65                  70                  75

TTA AAG ACC ATC CAG GAG GTG GCT GGT TAT GTC CTC ATT GCC CTC AAC    468
Leu Lys Thr Ile Gln Glu Val Ala Gly Tyr Val Leu Ile Ala Leu Asn
     80                  85                  90

ACA GTG GAG CGA ATT CCT TTG GAA AAC CTG CAG ATC ATC AGA GGA AAT    516
Thr Val Glu Arg Ile Pro Leu Glu Asn Leu Gln Ile Ile Arg Gly Asn
 95                 100                 105                 110

ATG TAC TAC GAA AAT TCC TAT GCC TTA GCA GTC TTA TCT AAC TAT GAT    564
Met Tyr Tyr Glu Asn Ser Tyr Ala Leu Ala Val Leu Ser Asn Tyr Asp
                115                 120                 125

GCA AAT AAA ACC GGA CTG AAG GAG CTG CCC ATG AGA AAT TTA CAG GAA    612
Ala Asn Lys Thr Gly Leu Lys Glu Leu Pro Met Arg Asn Leu Gln Glu
            130                 135                 140

ATC CTG CAT GGC GCC GTG CGG TTC AGC AAC AAC CCT GCC CTG TGC AAC    660
Ile Leu His Gly Ala Val Arg Phe Ser Asn Asn Pro Ala Leu Cys Asn
        145                 150                 155
```

-continued

```
GTG GAG AGC ATC CAG TGG CGG GAC ATA GTC AGC AGT GAC TTT CTC AGC      708
Val Glu Ser Ile Gln Trp Arg Asp Ile Val Ser Ser Asp Phe Leu Ser
160                     165                 170

AAC ATG TCG ATG GAC TTC CAG AAC CAC CTG GGC AGC TGC CAA AAG TGT      756
Asn Met Ser Met Asp Phe Gln Asn His Leu Gly Ser Cys Gln Lys Cys
175                     180                 185                 190

GAT CCA AGC TGT CCC AAT GGG AGC TGC TGG GGT GCA GGA GAG GAG AAC      804
Asp Pro Ser Cys Pro Asn Gly Ser Cys Trp Gly Ala Gly Glu Glu Asn
                195                 200                 205

TGC CAG AAA CTG ACC AAA ATC ATC TGT GCC CAG CAG TGC TCC GGG CGC      852
Cys Gln Lys Leu Thr Lys Ile Ile Cys Ala Gln Gln Cys Ser Gly Arg
210                 215                 220

TGC CGT GGC AAG TCC CCC AGT GAC TGC TGC CAC AAC CAG TGT GCT GCA      900
Cys Arg Gly Lys Ser Pro Ser Asp Cys Cys His Asn Gln Cys Ala Ala
            225                 230                 235

GGC TGC ACA GGC CCC CGG GAG AGC GAC TGC CTG GTC TGC CGC AAA TTC      948
Gly Cys Thr Gly Pro Arg Glu Ser Asp Cys Leu Val Cys Arg Lys Phe
240                 245                 250

CGA GAC GAA GCC ACG TGC AAG GAC ACC TGC CCC CCA CTC ATG CTC TAC      996
Arg Asp Glu Ala Thr Cys Lys Asp Thr Cys Pro Pro Leu Met Leu Tyr
255                 260                 265                 270

AAC CCC ACC ACG TAC CAG ATG GAT GTG AAC CCC GAG GGC AAA TAC AGC     1044
Asn Pro Thr Thr Tyr Gln Met Asp Val Asn Pro Glu Gly Lys Tyr Ser
                275                 280                 285

TTT GGT GCC ACC TGC GTG AAG AAG TGT CCC CGT AAT TAT GTG GTG ACA     1092
Phe Gly Ala Thr Cys Val Lys Lys Cys Pro Arg Asn Tyr Val Val Thr
            290                 295                 300

GAT CAC GGC TCG TGC GTC CGA GCC TGT GGG GCC GAC AGC TAT GAG ATG     1140
Asp His Gly Ser Cys Val Arg Ala Cys Gly Ala Asp Ser Tyr Glu Met
            305                 310                 315

GAG GAA GAC GGC GTC CGC AAG TGT AAG AAG TGC GAA GGG CCT TGC CGC     1188
Glu Glu Asp Gly Val Arg Lys Cys Lys Lys Cys Glu Gly Pro Cys Arg
320                 325                 330

AAA GTG TGT AAC GGA ATA GGT ATT GGT GAA TTT AAA GAC TCA CTC TCC     1236
Lys Val Cys Asn Gly Ile Gly Ile Gly Glu Phe Lys Asp Ser Leu Ser
335                 340                 345                 350

ATA AAT GCT ACG AAT ATT AAA CAC TTC AAA AAC TGC ACC TCC ATC AGT     1284
Ile Asn Ala Thr Asn Ile Lys His Phe Lys Asn Cys Thr Ser Ile Ser
                355                 360                 365

GGC GAT CTC CAC ATC CTG CCG GTG GCA TTT AGG GGT GAC TCC TTC ACA     1332
Gly Asp Leu His Ile Leu Pro Val Ala Phe Arg Gly Asp Ser Phe Thr
            370                 375                 380

CAT ACT CCT CCT CTG GAT CCA CAG GAA CTG GAT ATT CTG AAA ACC GTA     1380
His Thr Pro Pro Leu Asp Pro Gln Glu Leu Asp Ile Leu Lys Thr Val
            385                 390                 395

AAG GAA ATC ACA GGG TTT TTG CTG ATT CAG GCT TGG CCT GAA AAC AGG     1428
Lys Glu Ile Thr Gly Phe Leu Leu Ile Gln Ala Trp Pro Glu Asn Arg
400                 405                 410

ACG GAC CTC CAT GCC TTT GAG AAC CTA GAA ATC ATA CGC GGC AGG ACC     1476
Thr Asp Leu His Ala Phe Glu Asn Leu Glu Ile Ile Arg Gly Arg Thr
415                 420                 425                 430

AAG CAA CAT GGT CAG TTT TCT CTT GCA GTC GTC AGC CTG AAC ATA ACA     1524
Lys Gln His Gly Gln Phe Ser Leu Ala Val Val Ser Leu Asn Ile Thr
                435                 440                 445

TCC TTG GGA TTA CGC TCC CTC AAG GAG ATA AGT GAT GGA GAT GTG ATA     1572
Ser Leu Gly Leu Arg Ser Leu Lys Glu Ile Ser Asp Gly Asp Val Ile
            450                 455                 460

ATT TCA GGA AAC AAA AAT TTG TGC TAT GCA AAT ACA ATA AAC TGG AAA     1620
Ile Ser Gly Asn Lys Asn Leu Cys Tyr Ala Asn Thr Ile Asn Trp Lys
            465                 470                 475
```

-continued

| | | |
|---|---|---|
| AAA CTG TTT GGG ACC TCC GGT CAG AAA ACC AAA ATT ATA AGC AAC AGA<br>Lys Leu Phe Gly Thr Ser Gly Gln Lys Thr Lys Ile Ile Ser Asn Arg<br>480                          485                  490 | | 1668 |
| GGT GAA AAC AGC TGC AAG GCC ACA GGC CAG GTC TGC CAT GCC TTG TGC<br>Gly Glu Asn Ser Cys Lys Ala Thr Gly Gln Val Cys His Ala Leu Cys<br>495                          500                  505                  510 | | 1716 |
| TCC CCC GAG GGC TGC TGG GGC CCG GAG CCC AGG GAC TGC GTC TCT TGC<br>Ser Pro Glu Gly Cys Trp Gly Pro Glu Pro Arg Asp Cys Val Ser Cys<br>                         515                  520                  525 | | 1764 |
| CGG AAT GTC AGC CGA GGC AGG GAA TGC GTG GAC AAG TGC AAG CTT CTG<br>Arg Asn Val Ser Arg Gly Arg Glu Cys Val Asp Lys Cys Lys Leu Leu<br>                 530                  535                  540 | | 1812 |
| GAG GGT GAG CCA AGG GAG TTT GTG GAG AAC TCT GAG TGC ATA CAG TGC<br>Glu Gly Glu Pro Arg Glu Phe Val Glu Asn Ser Glu Cys Ile Gln Cys<br>                 545                  550                  555 | | 1860 |
| CAC CCA GAG TGC CTG CCT CAG GCC ATG AAC ATC ACC TGC ACA GGA CGG<br>His Pro Glu Cys Leu Pro Gln Ala Met Asn Ile Thr Cys Thr Gly Arg<br>560                          565                  570 | | 1908 |
| GGA CCA GAC AAC TGT ATC CAG TGT GCC CAC TAC ATT GAC GGC CCC CAC<br>Gly Pro Asp Asn Cys Ile Gln Cys Ala His Tyr Ile Asp Gly Pro His<br>575                          580                  585                  590 | | 1956 |
| TGC GTC AAG ACC TGC CCG GCA GGA GTC ATG GGA GAA AAC AAC ACC CTG<br>Cys Val Lys Thr Cys Pro Ala Gly Val Met Gly Glu Asn Asn Thr Leu<br>                 595                  600                  605 | | 2004 |
| GTC TGG AAG TAC GCA GAC GCC GGC CAT GTG TGC CAC CTG TGC CAT CCA<br>Val Trp Lys Tyr Ala Asp Ala Gly His Val Cys His Leu Cys His Pro<br>                 610                  615                  620 | | 2052 |
| AAC TGC ACC TAC GGA TGC ACT GGG CCA GGT CTT GAA GGC TGT CCA ACG<br>Asn Cys Thr Tyr Gly Cys Thr Gly Pro Gly Leu Glu Gly Cys Pro Thr<br>                 625                  630                  635 | | 2100 |
| AAT GGG CCT AAG ATC CCG TCC ATC GCC ACT GGG ATG GTG GGG GCC CTC<br>Asn Gly Pro Lys Ile Pro Ser Ile Ala Thr Gly Met Val Gly Ala Leu<br>640                          645                  650 | | 2148 |
| CTC TTG CTG CTG GTG GTG GCC CTG GGG ATC GGC CTC TTC ATG CGA AGG<br>Leu Leu Leu Leu Val Val Ala Leu Gly Ile Gly Leu Phe Met Arg Arg<br>655                          660                  665                  670 | | 2196 |
| CGC CAC ATC GTT CGG AAG CGC ACG CTG CGG AGG CTG CTG CAG GAG AGG<br>Arg His Ile Val Arg Lys Arg Thr Leu Arg Arg Leu Leu Gln Glu Arg<br>                 675                  680                  685 | | 2244 |
| GAG CTT GTG GAG CCT CTT ACA CCC AGT GGA GAA GCT CCC AAC CAA GCT<br>Glu Leu Val Glu Pro Leu Thr Pro Ser Gly Glu Ala Pro Asn Gln Ala<br>                 690                  695                  700 | | 2292 |
| CTC TTG AGG ATC TTG AAG GAA ACT GAA TTC AAA AAG ATC AAA GTG CTG<br>Leu Leu Arg Ile Leu Lys Glu Thr Glu Phe Lys Lys Ile Lys Val Leu<br>705                          710                  715 | | 2340 |
| GGC TCC GGT GCG TTC GGC ACG GTG TAT AAG GGA CTC TGG ATC CCA GAA<br>Gly Ser Gly Ala Phe Gly Thr Val Tyr Lys Gly Leu Trp Ile Pro Glu<br>720                          725                  730 | | 2388 |
| GGT GAG AAA GTT AAA ATT CCC GTC GCT ATC AAG GAA TTA AGA GAA GCA<br>Gly Glu Lys Val Lys Ile Pro Val Ala Ile Lys Glu Leu Arg Glu Ala<br>735                          740                  745                  750 | | 2436 |
| ACA TCT CCG AAA GCC AAC AAG GAA ATC CTC GAT GAA GCC TAC GTG ATG<br>Thr Ser Pro Lys Ala Asn Lys Glu Ile Leu Asp Glu Ala Tyr Val Met<br>                 755                  760                  765 | | 2484 |
| GCC AGC GTG GAC AAC CCC CAC GTG TGC CGC CTG CTG GGC ATC TGC CTC<br>Ala Ser Val Asp Asn Pro His Val Cys Arg Leu Leu Gly Ile Cys Leu<br>                 770                  775                  780 | | 2532 |
| ACC TCC ACC GTG CAA CTC ATC ACG CAG CTC ATG CCC TTC GGC TGC CTC<br>Thr Ser Thr Val Gln Leu Ile Thr Gln Leu Met Pro Phe Gly Cys Leu<br>785                          790                  795 | | 2580 |

```
CTG GAC TAT GTC CGG GAA CAC AAA GAC AAT ATT GGC TCC CAG TAC CTG         2628
Leu Asp Tyr Val Arg Glu His Lys Asp Asn Ile Gly Ser Gln Tyr Leu
    800                 805                 810

CTC AAC TGG TGT GTG CAG ATC GCA AAG GGC ATG AAC TAC TTG GAG GAC         2676
Leu Asn Trp Cys Val Gln Ile Ala Lys Gly Met Asn Tyr Leu Glu Asp
815                 820                 825                 830

CGT CGC TTG GTG CAC CGC GAC CTG GCA GCC AGG AAC GTA CTG GTG AAA         2724
Arg Arg Leu Val His Arg Asp Leu Ala Ala Arg Asn Val Leu Val Lys
                835                 840                 845

ACA CCG CAG CAT GTC AAG ATC ACA GAT TTT GGG CTG GCC AAA CTG CTG         2772
Thr Pro Gln His Val Lys Ile Thr Asp Phe Gly Leu Ala Lys Leu Leu
            850                 855                 860

GGT GCG GAA GAG AAA GAA TAC CAT GCA GAA GGA GGC AAA GTG CCT ATC         2820
Gly Ala Glu Glu Lys Glu Tyr His Ala Glu Gly Gly Lys Val Pro Ile
        865                 870                 875

AAG TGG ATG GCA TTG GAA TCA ATT TTA CAC AGA ATC TAT ACC CAC CAG         2868
Lys Trp Met Ala Leu Glu Ser Ile Leu His Arg Ile Tyr Thr His Gln
880                 885                 890

AGT GAT GTC TGG AGC TAC GGG GTG ACC GTT TGG GAG TTG ATG ACC TTT         2916
Ser Asp Val Trp Ser Tyr Gly Val Thr Val Trp Glu Leu Met Thr Phe
895                 900                 905                 910

GGA TCC AAG CCA TAT GAC GGA ATC CCT GCC AGC GAG ATC TCC TCC ATC         2964
Gly Ser Lys Pro Tyr Asp Gly Ile Pro Ala Ser Glu Ile Ser Ser Ile
                915                 920                 925

CTG GAG AAA GGA GAA CGC CTC CCT CAG CCA CCC ATA TGT ACC ATC GAT         3012
Leu Glu Lys Gly Glu Arg Leu Pro Gln Pro Pro Ile Cys Thr Ile Asp
            930                 935                 940

GTC TAC ATG ATC ATG GTC AAG TGC TGG ATG ATA GAC GCA GAT AGT CGC         3060
Val Tyr Met Ile Met Val Lys Cys Trp Met Ile Asp Ala Asp Ser Arg
        945                 950                 955

CCA AAG TTC CGT GAG TTG ATC ATC GAA TTC TCC AAA ATG GCC CGA GAC         3108
Pro Lys Phe Arg Glu Leu Ile Ile Glu Phe Ser Lys Met Ala Arg Asp
960                 965                 970

CCC CAG CGC TAC CTT GTC ATT CAG GGG GAT GAA AGA ATG CAT TTG CCA         3156
Pro Gln Arg Tyr Leu Val Ile Gln Gly Asp Glu Arg Met His Leu Pro
975                 980                 985                 990

AGT CCT ACA GAC TCC AAC TTC TAC CGT GCC CTG ATG GAT GAA GAA GAC         3204
Ser Pro Thr Asp Ser Asn Phe Tyr Arg Ala Leu Met Asp Glu Glu Asp
                995                 1000                1005

ATG GAC GAC GTG GTG GAT GCC GAC GAG TAC CTC ATC CCA CAG CAG GGC         3252
Met Asp Asp Val Val Asp Ala Asp Glu Tyr Leu Ile Pro Gln Gln Gly
            1010                1015                1020

TTC TTC AGC AGC CCC TCC ACG TCA CGG ACT CCC CTC CTG AGC TCT CTG         3300
Phe Phe Ser Ser Pro Ser Thr Ser Arg Thr Pro Leu Leu Ser Ser Leu
        1025                1030                1035

AGT GCA ACC AGC AAC AAT TCC ACC GTG GCT TGC ATT GAT AGA AAT GGG         3348
Ser Ala Thr Ser Asn Asn Ser Thr Val Ala Cys Ile Asp Arg Asn Gly
1040                1045                1050

CTG CAA AGC TGT CCC ATC AAG GAA GAC AGC TTC TTG CAG CGA TAC AGC         3396
Leu Gln Ser Cys Pro Ile Lys Glu Asp Ser Phe Leu Gln Arg Tyr Ser
1055                1060                1065                1070

TCA GAC CCC ACA GGC GCC TTG ACT GAG GAC AGC ATA GAC GAC ACC TTC         3444
Ser Asp Pro Thr Gly Ala Leu Thr Glu Asp Ser Ile Asp Asp Thr Phe
                1075                1080                1085

CTC CCA GTG CCT GAA TAC ATA AAC CAG TCC GTT CCC AAA AGG CCC GCT         3492
Leu Pro Val Pro Glu Tyr Ile Asn Gln Ser Val Pro Lys Arg Pro Ala
            1090                1095                1100

GGC TCT GTG CAG AAT CCT GTC TAT CAC AAT CAG CCT CTG AAC CCC GCG         3540
Gly Ser Val Gln Asn Pro Val Tyr His Asn Gln Pro Leu Asn Pro Ala
        1105                1110                1115
```

| | |
|---|---|
| CCC AGC AGA GAC CCA CAC TAC CAG GAC CCC CAC AGC ACT GCA GTG GGC<br>Pro Ser Arg Asp Pro His Tyr Gln Asp Pro His Ser Thr Ala Val Gly<br>    1120                                 1125                             1130 | 3588 |
| AAC CCC GAG TAT CTC AAC ACT GTC CAG CCC ACC TGT GTC AAC AGC ACA<br>Asn Pro Glu Tyr Leu Asn Thr Val Gln Pro Thr Cys Val Asn Ser Thr<br>1135                            1140                         1145                         1150 | 3636 |
| TTC GAC AGC CCT GCC CAC TGG GCC CAG AAA GGC AGC CAC CAA ATT AGC<br>Phe Asp Ser Pro Ala His Trp Ala Gln Lys Gly Ser His Gln Ile Ser<br>                1155                         1160                         1165 | 3684 |
| CTG GAC AAC CCT GAC TAC CAG CAG GAC TTC TTT CCC AAG GAA GCC AAG<br>Leu Asp Asn Pro Asp Tyr Gln Gln Asp Phe Phe Pro Lys Glu Ala Lys<br>                      1170                         1175                         1180 | 3732 |
| CCA AAT GGC ATC TTT AAG GGC TCC ACA GCT GAA AAT GCA GAA TAC CTA<br>Pro Asn Gly Ile Phe Lys Gly Ser Thr Ala Glu Asn Ala Glu Tyr Leu<br>                1185                         1190                         1195 | 3780 |
| AGG GTC GCG CCA CAA AGC AGT GAA TTT ATT GGA GCA TGACCACGGA<br>Arg Val Ala Pro Gln Ser Ser Glu Phe Ile Gly Ala<br>                1200                         1205                         1210 | 3826 |
| GGATAGTATG AGCCCTAAAA ATCCAGACTC TTTCGATACC CAGGACCAAG CCACAGCAGG | 3886 |
| TCCTCCATCC CAACAGCCAT GCCCGCATTA GCTCTTAGAC CCACAGACTG GTTTTGCAAC | 3946 |
| GTTTACACCG ACTAGCCAGG AAGTACTTCC ACCTCGGGCA CATTTTGGGA AGTTGCATTC | 4006 |
| CTTTGTCTTC AAACTGTGAA GCATTTACAG AAACGCATCC AGCAAGAATA TTGTCCCTTT | 4066 |
| GAGCAGAAAT TTATCTTTCA AGAGGTATA TTTGAAAAAA AAAAAAAAAG TATATGTGAG | 4126 |
| GATTTTTATT GATTGGGGAT CTTGGAGTTT TTCATTGTCG CTATTGATTT TTACTTCAAT | 4186 |
| GGGCTCTTCC AACAAGGAAG AAGCTTGCTG GTAGCACTTG CTACCCTGAG TTCATCCAGG | 4246 |
| CCCAACTGTG AGCAAGGAGC ACAAGCCACA AGTCTTCCAG AGGATGCTTG ATTCCAGTGG | 4306 |
| TTCTGCTTCA AGGCTTCCAC TGCAAAACAC TAAAGATCCA AGAAGGCCTT CATGGCCCCA | 4366 |
| GCAGGCCGGA TCGGTACTGT ATCAAGTCAT GGCAGGTACA GTAGGATAAG CCACTCTGTC | 4426 |
| CCTTCCTGGG CAAAGAAGAA ACGGAGGGGA TGAATTCTTC CTTAGACTTA CTTTTGTAAA | 4486 |
| AATGTCCCCA CGGTACTTAC TCCCCACTGA TGGACCAGTG GTTTCCAGTC ATGAGCGTTA | 4546 |
| GACTGACTTG TTTGTCTTCC ATTCCATTGT TTTGAAACTC AGTATGCCGC CCCTGTCTTG | 4606 |
| CTGTCATGAA ATCAGCAAGA GAGGATGACA CATCAAATAA TAACTCGGAT CCAGCCCAC | 4666 |
| ATTGGATTCA TCAGCATTTG GACCAATAGC CCACAGCTGA GAATGTGGAA TACCTAAGGA | 4726 |
| TAACACCGCT TTTGTTCTCG CAAAAACGTA TCTCCTAATT TGAGGCTCAG ATGAAATGCA | 4786 |
| TCAGGTCCTT TGGGGCATAG ATCAGAAGAC TACAAAAATG AAGCTGCTCT GAAATCTCCT | 4846 |
| TTAGCCATCA CCCCAACCCC CCAAAATTAG TTTGTGTTAC TTATGGAAGA TAGTTTTCTC | 4906 |
| CTTTTACTTC ACTTCAAAAG CTTTTTACTC AAAGAGTATA TGTTCCCTCC AGGTCAGCTG | 4966 |
| CCCCCAAACC CCCTCCTTAC GCTTTGTCAC ACAAAAAGTG TCTCTGCCTT GAGTCATCTA | 5026 |
| TTCAAGCACT TACAGCTCTG GCCACAACAG GGCATTTTAC AGGTGCGAAT GACAGTAGCA | 5086 |
| TTATGAGTAG TGTGAATTCA GGTAGTAAAT ATGAAACTAG GGTTTGAAAT TGATAATGCT | 5146 |
| TTCACAACAT TTGCAGATGT TTTAGAAGGA AAAAGTTCC TTCCTAAAAT AATTTCTCTA | 5206 |
| CAATTGGAAG ATTGGAAGAT TCAGCTAGTT AGGAGCCCAT TTTTTCCTAA TCTGTGTGTG | 5266 |
| CCCTGTAACC TGACTGGTTA ACAGCAGTCC TTTGTAAACA GTGTTTTAAA CTCTCCTAGT | 5326 |
| CAATATCCAC CCCATCCAAT TTATCAAGGA AGAAATGGTT CAGAAAATAT TTTCAGCCTA | 5386 |
| CAGTTATGTT CAGTCACACA CACATACAAA ATGTTCCTTT TGCTTTTAAA GTAATTTTTG | 5446 |
| ACTCCCAGAT CAGTCAGAGC CCCTACAGCA TTGTTAAGAA AGTATTTGAT TTTTGTCTCA | 5506 |

ATGAAAATAA AACTATATTC ATTTCC                                                    5532

(2) INFORMATION FOR SEQ ID NO:4:

(i) SEQUENCE CHARACTERISTICS:
        (A) LENGTH: 1210 amino acids
        (B) TYPE: amino acid
        (D) TOPOLOGY: linear (ii) MOLECULE TYPE: protein (xi) SEQUENCE DESCRIPTION: SEQ ID NO:4:

Met Arg Pro Ser Gly Thr Ala Gly Ala Ala Leu Leu Ala Leu Leu Ala
 1               5                  10                  15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

```
Ala Thr Asn Ile Lys His Phe Lys Asn Cys Thr Ser Ile Ser Gly Asp
             355                 360                 365

Leu His Ile Leu Pro Val Ala Phe Arg Gly Asp Ser Phe Thr His Thr
         370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
             405                 410                 415

Leu His Ala Phe Glu Asn Leu Glu Ile Ile Arg Gly Arg Thr Lys Gln
         420                 425                 430

His Gly Gln Phe Ser Leu Ala Val Val Ser Leu Asn Ile Thr Ser Leu
         435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
             485                 490                 495

Asn Ser Cys Lys Ala Thr Gly Gln Val Cys His Ala Leu Cys Ser Pro
             500                 505                 510

Glu Gly Cys Trp Gly Pro Glu Pro Arg Asp Cys Val Ser Cys Arg Asn
             515                 520                 525

Val Ser Arg Gly Arg Glu Cys Val Asp Lys Cys Lys Leu Leu Glu Gly
         530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
             565                 570                 575

Asp Asn Cys Ile Gln Cys Ala His Tyr Ile Asp Gly Pro His Cys Val
             580                 585                 590

Lys Thr Cys Pro Ala Gly Val Met Gly Glu Asn Asn Thr Leu Val Trp
         595                 600                 605

Lys Tyr Ala Asp Ala Gly His Val Cys His Leu Cys His Pro Asn Cys
         610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
             645                 650                 655

Leu Leu Val Val Ala Leu Gly Ile Gly Leu Phe Met Arg Arg Arg His
         660                 665                 670

Ile Val Arg Lys Arg Thr Leu Arg Arg Leu Leu Gln Glu Arg Glu Leu
         675                 680                 685

Val Glu Pro Leu Thr Pro Ser Gly Glu Ala Pro Asn Gln Ala Leu Leu
         690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
             725                 730                 735

Lys Val Lys Ile Pro Val Ala Ile Lys Glu Leu Arg Glu Ala Thr Ser
             740                 745                 750

Pro Lys Ala Asn Lys Glu Ile Leu Asp Glu Ala Tyr Val Met Ala Ser
             755                 760                 765
```

-continued

```
Val Asp Asn Pro His Val Cys Arg Leu Leu Gly Ile Cys Leu Thr Ser
770             775                 780
Thr Val Gln Leu Ile Thr Gln Leu Met Pro Phe Gly Cys Leu Leu Asp
785             790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
            820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
        850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
                900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala Leu Met Asp Glu Glu Asp Met Asp
        995                 1000                1005
Asp Val Val Asp Ala Asp Glu Tyr Leu Ile Pro Gln Gln Gly Phe Phe
    1010                1015                1020
Ser Ser Pro Ser Thr Ser Arg Thr Pro Leu Leu Ser Ser Leu Ser Ala
1025                1030                1035                1040
Thr Ser Asn Asn Ser Thr Val Ala Cys Ile Asp Arg Asn Gly Leu Gln
                1045                1050                1055
Ser Cys Pro Ile Lys Glu Asp Ser Phe Leu Gln Arg Tyr Ser Ser Asp
            1060                1065                1070
Pro Thr Gly Ala Leu Thr Glu Asp Ser Ile Asp Asp Thr Phe Leu Pro
        1075                1080                1085
Val Pro Glu Tyr Ile Asn Gln Ser Val Pro Lys Arg Pro Ala Gly Ser
    1090                1095                1100
Val Gln Asn Pro Val Tyr His Asn Gln Pro Leu Asn Pro Ala Pro Ser
1105                1110                1115                1120
Arg Asp Pro His Tyr Gln Asp Pro His Ser Thr Ala Val Gly Asn Pro
                1125                1130                1135
Glu Tyr Leu Asn Thr Val Gln Pro Thr Cys Val Asn Ser Thr Phe Asp
            1140                1145                1150
Ser Pro Ala His Trp Ala Gln Lys Gly Ser His Gln Ile Ser Leu Asp
        1155                1160                1165
Asn Pro Asp Tyr Gln Gln Asp Phe Phe Pro Lys Glu Ala Lys Pro Asn
    1170                1175                1180
```

-continued

```
Gly Ile Phe Lys Gly Ser Thr Ala Glu Asn Ala Glu Tyr Leu Arg Val
1185             1190            1195                1200

Ala Pro Gln Ser Ser Glu Phe Ile Gly Ala
                1205            1210
```

ERBB-2 GENE SEGMENTS, PROBES, RECOMBINANT DNA AND KITS FOR DETECTION

This application is a division of application Ser. No. 07/786,598, filed Nov. 1, 1991, now U.S. Pat. No. 5,747,261, issued May 5, 1998, which is a division of application Ser. No. 07/110,791, filed Oct. 21, 1987, which is a continuation-in-part of application Ser. No. 06/836,414 filed Mar. 5, 1986 (now abandoned).

BACKGROUND OF THE INVENTION

1. Technical Field

The present invention is related to the cloning, isolation and partial characterization of a hitherto unidentified human gene. More particularly, the present invention is related to the preparation and identification of a v-erbB related human gene that is a new member of the tyrosine kinase encoding family of genes and is amplified in a human mammary carcinoma.

2. State of the Art

A number of genes have been identified as retroviral oncogenes that are responsible for inducing tumors in vivo and transforming cells in vitro (Land et al., *Science* 222:771–778, 1983). Some of them apparently encode transforming proteins 9that share a kinase domain homologous to that of $pp60^{src}$ a tyrosine-specific protein kinase. The cellular cognate, encoded by the c-src gene, also exhibits tyrosine-specific kinase activity. Of particular interest is the fact that tyrosine-specific kinases are also encoded by other genes for several receptors for polypeptide growth factors, including the receptors for epidermal growth factor (EGF) (Cohen et al., *J Biol. Chem.* 255:4834–4842, 1980), platelet-derived growth factor (PDGF) (Nishimura et al., *Proc. Natl. Acad Sci.* USA 79:4303–4307, 1982), insulin (Kasuga et al., *Nature* 298:667–669, 1982), and insulin-like growth factor I (Rubin et al., *Nature* 305:438–440, 1983). This implies a possible link between the action of the growth factor-receptor complex and the oncogene products with tyrosine-specific kinase activity.

Recent analysis of the v-erbB gene and the EGF receptor gene indicates that the v-erbB gene is a part of the EGF receptor gene and codes for the internal domain and transmembrane portion of the receptor (Yamamoto et al., *Cell* 35:71–78, 1983; Downward et al., *Nature* 307:521–527, 1984; Ullrich et al., *Nature* 309:418–425, 1984). These findings, together with the extensive identity of the amino acid sequences of the v-sis protein and platelet-derived growth factor (Waterfield et al., *Nature* 304:35–39, 1983; Doolittle et al., *Science* 221:275–277, 1983), suggest that some viral oncogene products mimic the action of the polypeptide growth factor-receptor complex in activating a cellular pathway involved in cell proliferation and tumor formation.

Genetic alterations affecting proto-oncogenes of the tyrosine kinase family may play a role in spontaneous tumor development. A specific translocation affecting the c-abl locus, for example, is associated with chronic myelogenous leukemia (de Klein et al., *Nature* 300:765, 1982; Collins et al., *Proc. Natl. Acad Sci.* USA 80:4813, 1983). Several recent studies have also documented amplification or rearrangement of the gene for the EGF receptor in certain human tumors (Libermann et al., *Nature* 313:144, 1985), or tumor cell lines (Ulrich et al., *Nature* 309:418, 1984; Lin et al., *Science* 224:843, 1984). However, a gene that is a new member of the tyrosine kinase family and is amplified in a human mammary carcinoma and is closely related to, but distinct from the EGF receptor gene, has not heretofore been known.

SUMMARY OF THE INVENTION

It is, therefore, an object of the present invention to provide a novel, cloned, human gene having the nucleotide sequene (SEQ ID NO:2) as shown in FIG. 1 and described more fully herein infra.

It is a fuirther object of the present invention to provide products, e.g. various RNAs and/or polyp eptides encoded by the cloned gene.

It is a still further object of the present invention to provide antibodies, either polydlonal or monoclonal, directed against the protein product encoded by said gene and a diagnostic kit containing said antibodies for the detection of carcinomas.

It is another object of the present invention to provide complementary DNA (cDNA) clones homologous to the messenger RNA (mRNA) encoded by the cloned gene, said cDNA clones being capable of expressing large amounts of corresponding protein in a heterologous vector system, such as bacteria, yeast, eukaryotes and the like.

It is yet another object of the present invention to produce a transformed cell or organism capable of expressing said gene by incorporating said gene or a part thereof into the genome of said cell, vector or organism.

It is a still further object of the present invention to provide nucleic acid probes and/or antibody reagent kits capable of detecting said gene or a product thereof.

Other objects and advantages of the present invention will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 3 shows a comparison of the putative encoded amino acid sequence of various polypeptide products, and comparison of the putative encoded amino acid sequence in pMAC117 with known tyrosine kinase sequences. Black regions represent homologous amino acids. Differing amino acid residues are shown in one letter code (A, alanine; C. cysteine, D. aspartic acid; E. glutamic acid; F. phenylalanine; G. glycine; H. histidine; I. isoleucine; K. lysine; L. leucine; M. methionine; N. asparagine; P. proline; Q. glutamine; R. arginine; S. serine; T. threonine; V. valine; W. tryptophan; Y. tyrosine). Amino acid positions conserved in all sequences are denoted by *. The tyrosine homologous to that autophosphorylated by the v-src protein (Smart et al., *Proc. Natl. Acad Sci.* USA 78:6013, 1981) is shown by an arrow. The v-abl sequence contains a tyrosine residue in this region displaced by two positions. The amino acid sequences of human EGF receptor, v-src, v-abl, v-fms, and human insulin receptor were aligned by the computer program described by Ullrich et al. (*Nature* 313:756, 1985) which is incorporated herein by reference. As disclosed in Ullrich et al. (1984), the nucleotide sequence, with the corresponding amino acid sequence of the EGF receptor gene is set forth in SEQ ID NO:3. As fuirther disclosed in Ullrich et al. (1984), the amino acid sequence encoded by the EGF receptor gene is set forth in SEQ ID NO:4. The homology observed with the predicted amino acid sequence of v-yes and v-fes was 51 percent and 48 percent, respectively.

FIG. 5A shows the restriction map of complementary DNA of MAC117 encompassing the entire coding region of the gene. Clone pMAC137 was isolated from an oligo dT primed normal human fibroblast cDNA library (Okyama et al., *Mol. Cell. Biol.* 3:280, 1983) using a 0.8-kbp Acc I fragment from the 3' terminus of pMAC117 as probe. Clones λMAC30, λMAC10', and λMAC14-1 were subsequently isolated from a randomly primed MCF-7 cDNA library (Walter et al., *Proc. Natl. Acad Sci.* USA, 82:7889, 1985) using cDNA fragments as probes. Restriction sites: B-Bam, BII-Bst EII, E-Eco RI, N-NCO I, P-Pst I, Sm-Sma I, Sp-Sph I, and St-Stu I.

FIG. 5B illustrates three probes, a, b, and c, representing the 5' end, a middle portion, and the entire coding region, respectively, which were employed in subsequent studies elucidating the role and function of this v-erbB-related gene.

DETAILED DESCRIPTION OF INVENTION

Figure 1:
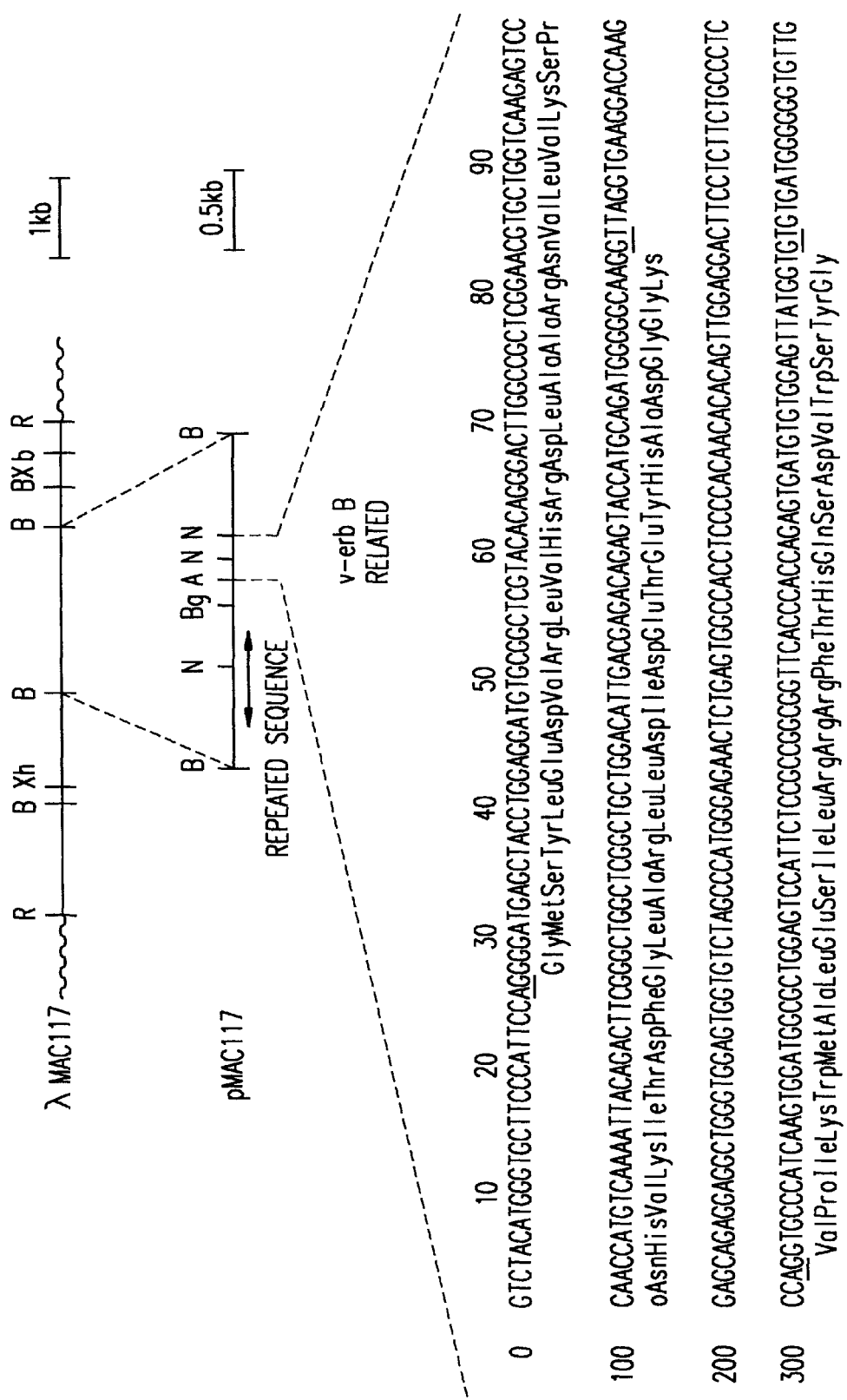
FIG. 1 shows a characteristic fragment produced by Eco RI restriction of the cloned gene of the present invention: the restriction-site map of λMAC117 and plasmid pMAC117. A: Acc I; B: Bam HI; Bg: Bgl I; N: Nco I; R: Eco RI; X: Xba I; Xh: Xho I. The sites were located by electrophoretic analysis of the products of single and double digestion. Regions homologous to v-erbB or human repetitive sequences (region flanked by arrows) were located by Southern blot hybridization (Southern, *J. Mol. Biol.* 98:503, 1975), with the v-erbB probe or total human DNA made radioactive by nick translation (Rigby etal., *J. Mol. Biol.* 113:237, 1977). Hybridization conditions were as described in FIG. 2. The nucleotide sequence (SEQ ID NO:2) of pMAC117 between the Acc I site and the Nco I sites and regions of encoded amino acid sequence homologous to the EGF receptor are shown. The AG or GT dinucleotides flanking the putative coding regions are underlined. To determine the sequence, Nco I, Hinf I and Sau 96 I fragments were labeled at the 3' termini by means of a large fragment of *E. coli* DNA polymerase, separated into single strands by gel electrophoresis and chemically degraded (Maxam et al., *Proc. Natl. Acad Sci.*, USA 74:560, 1977).

The above and other objects and advantages of the present invention are achieved by a cloned human gene having the nucleotide sequence SEQ ID NO: 2) as shown in FIG. 1. Although any methods and materials similar or equivalent to those described herein can be used in the practice or testing of the present invention, the preferred methods and materials are now described. All publications mentioned under the "Brief Description of Drawings" and hereunder are incorporated herein by reference. Unless defined otherwise, all technical or scientific terms used herein have the same meaning as commonly understood by one of ordinary skill in the art to which this invention belongs.

Cells and Tissues:

Preparation of High Molecular Weight DNA

1. From A431 cells:

A431 carcinoma cells were established in culture and maintained in Dulbecco's modified Eagle's medium with 10% fetal calf serum.

Cells were grown to 90% confluence in four 175cm$^2$ tissue culture flasks, washed twice with phosphate buffered saline (Gibco Biochemicals), then lysed in 10 mM Tris (pH 7.5), 150 mM NaCl, 50 mM ethylenediamine-tetraacetate (EDTA) and 0.5% sodium dodecyl sulfate (SDS) Proteinase K (Boerhinger Mannheim) was added to a concentration of 0.1 mg/ml and the cell extracts digested for 3 hours at 50° C. DNA was extracted 3 times with phenol and once with CHCl$_3$. DNA was precipitated with 2 volumes of ethanol, spooled and resuspended in 20 ml of 10 mM Tris-HCl (pH 7.5), 1 mM EDTA. The solution was then made 10 $\mu$g/ml with (DNase free) RNase (Boerhinger Mannheim) and incubated for 2 hr at 50° C. NaCl was added to 0.5M and the solution extracted with phenol followed by CHCl$_3$. DNA was precipitated in 10 mM Tris, 1 mM EDTA. The concentration was determined by routine spectrophotometric procedure at 260 nm wavelength.

2. From tissues:

Two grams original mass of primary tumor (designated MAC117 obtained from Memorial Sloan-Kettering Cancer Center Specimen code 31-26606) were pulverized in a mortar and pestle at liquid nitrogen temperature, suspended in 10 ml of 10 mM Tris-HCl (pH 7.5), 150 mM NaCl, 2 mM EDTA, reacted with proteinase K at 500 $\mu$g/ml (Boerhinger Mannheim) and SDS at 0.5% at 37° C. for 10 hr. The solution was then extracted twice with phenol and twice with the mixture of phenol:CHCl$_3$:isoamyl alcohol at 25:24:1 and once with CHCl$_3$:isoamyl alcohol (24:1). DNA was precipitated by 2 volumes of ethanol removed by spooling, and resuspended in 1 mM Tris-HCl (pH 7.5), 0.2 mM EDTA.

Electrophoretic Analysis of DNA Fragments Using "Southemn Hybridization"

1. Restriction enzyme cleavage

Each sample of DNA (15 $\mu$g) was digested in 0.4 ml of 100 mM Tris-HCl (pH 7.5), 50 mM NaCl, 5 mM MgCl$_2$, 100 $\mu$g/ml bovine serum albumin and 30 units of restriction enzyme (New England Biolabs) for 2 hr at 37° C. Following reaction, 10 $\mu$g of tRNA was added and the solution extracted once with an equal volume of a mixture of phenol and CHCl$_3$ (1:1). Nucleic acids were precipitated from the aqueous phase by addition of 2 volumes of ethanol. Following centrifuigation for 10 min at 12,000×g (Eppendorf microfuge) the samples were washed once with 80% ethanol, dried to remove ethanol, and resuspended in 40 $\mu$l distilled H$_2$O.

2. Agarose gel electrophoresis

DNA samples were made 40 mM Tris acetate (pH 7.2), 20 mM Na acetate, 1 mM EDTA, 5.0% glycerol, 0.05% bromophenol blue. Electrophoresis was conducted in a BRL H4 apparatus containing 400 ml 0.8% agarose, 40 mM Tris acetate (pH 7.2), 20 mM Na acetate, 1 mM EDTA and 1 $\mu$g/ml etbdium bromide for about 16 hr at about 50 volts following conventional procedure. DNA was detected by irradiation with ultraviolet light.

3. Transfer to nitrocellulose

The agarose gel was treated twice for 15 min in 1 liter of 0.5M NaOH 1.5M NaCl, then twice for 30 min with 1M NH$_4$Ac, 20 mM NaOH. The agarose gel was then placed on a stack of filter paper saturated with 1 liter of 1M NH$_4$Ac, 20mM NaOH. A sheet of nitrocellulose membrane (0.45 $\mu$m pore size, Schleicher & Schuesi) was placed on top of the gel followed by dry filter paper. Transfer was allowed to occur overnight. DNA was fixed to nitrocellulose by baking at 80° C. in vacuo for 2 hr.

Hybridization to RNA and DNA blots

Hybridization was conducted in 20 ml of 40% formamide, 0.75M NaCl, 0.075M Na citrate, 0.05% BSA, 0.05% polyvinyl pyrolidone, 0.05% Ficol 400 and 20 $\mu$g/ml sheared denatured calf thymus DNA. All hybridization was conducted for 16 hr at 42° C. in a water bath. Following hybridization, nitrocellulose membranes were washed 2 times for 20 min in 1 liter of 0.3M NaCl, 30 mM Na citrate, followed by washes in 15 mM NaCl, 1.5 mM Na citrate, first with and then without 0.1% sodium dodecyl sulfate. These final washes were at 42° C. for v-erbB probes and at 52° C. with pMAC117 and pE7 probes, vide infra. Autoradiography was conducted at −70° C. with Kodak XAR5 film. Exposure times were 2 hr for FIG. 2A and 20 min for FIG. 2B, 40 min for EGF receptor probe of FIG. 4, and 4 hr for the pMAC117 probe of FIG. 4.

Generation of probe DNAs

A nucleic acid probe is defined as a fragment of DNA or RNA whose nucleotide sequence has at least partial identity with the sequence of the gene or its messenger RNA so as to enable detection or identification of the gene. Since a gene may have several fragments, there could be a plurality of probes for detecting the gene.

The probes used were the 0.5-kb Bam HI to Bam HI fragment combined with the 0.5-kb Bam HI to Eco RI fragment of the v-erbB gene of AEV 11; the 1-kb BglI to Bam HI fragment of pMAC117; and the 2-kb Cla I fragment of pE7 as described by Xu, et al., (*Nature*, 309:806, 1984).

DNA fragments were isolated by gel electrophoresis in 1% low melting point agarose gels (Bethesda Research Labs) in 40 mM Tris acetate, 20 mM Na acetate, 1 mM EDTA, followed by melting of the gel at 70° C. and extraction with phenol followed by CHCl$_3$ and ethanol precipitation. DNAs were made radioactive by using a nick-translation kit (Amersham) in which 50 $\mu$l reactions contained 250 $\mu$Ci α-$^{32}$PdCTP (Amersham) and 0.5 $\mu$g DNA. Radioactive probe DNA was purified from unincorporated nucleotides by 2 cycles of ethanol precipitation.

Yields were above $2\times10^8$ cpm/μg DNA. Before hybridization all probes were made single-stranded by treatment with 90% formamide.

RNA electrophoresis and transfer to nitrocellulose

RNA samples (5 μg A431 polyadenylated RNA, obtained from National Institutes of Health, Bethesda, Md. 21218) were treated for 5 min at 50° C. in 50% formamide, 6.7% formaldehyde, 20 mM Mops (pH 7.0) (Sigma Biochemicals), 5 mM Na acetate, 1 mM EDTA in 25 μl total volume. Electrophoresis was conducted in BRL H4 apparatus in 250 ml of 1.5% agarose, 20 mM Mops (pH 7.0), 5 mM Na acetate, 1 mM EDTA, 1 μg/ml ethidium bromide at 40 volts for 16 hr. RNA was detected using ultraviolet light. The gel was soaked for 30 min at 20° C. in 50 mM NaOH followed by two 30 min washes in 1M Tris (pH 7.5), followed by 30 min in 3M NaCl, 0.3M Na citrate. Transfer to nitro-cellulose was accomplished by placing the gel atop a stack of filter paper saturated with 1.5M NaCl, 0.15M Na citrate, followed by 0.45 μM pore size nitrocellulose (Schleicher and Schuell), followed by dry filter paper. Transfer was allowed to proceed for 16 hr. The nitrocellulose filter was washed twice for 20 min in 0.3M NaCl, 30 mM Na citrate. RNA was fixed to the paper by baking at 80° C. in vacuo for 2 hr.

DNA sequence analysis

DNA fragments containing the Acc I-Nco I region (FIG. 1) were digested with either Nco I, Hinf I or Sau 96I (New England Biolabs). These fragments were end-labeled in reactions of 50 μl containing 50 mM Tris-HCl (pH 7.2), 10 mM $MgCl_2$, 0.1 mM dithiothreitol, 50 μg/ml BSA, 10 μCi α-$^{32}$PdXTP (Amersham—where X represents the correct nucleotide for fill-in), 2 units E. coli DNA polymerase large fragment (New England Biolabs). Following labeling, single-stranded material was prepared by electrophoresis. Samples were denatured in 30% dimethyl sulfoxide, 1 mM EDTA and 0.05% bromophenol blue at 90° C. for 2 hr. Samples were chilled and electrophoresed in acrylamide gels in a Bethesda Research Labs apparatus. DNA was detected by autoradiography and isolated by elution into 10 mM Tris-HCl (pH 7.0), 1 mM EDTA. Chemical degradation of DNA for sequence analysis was conducted using standard procedures. Cleavage at guanine (G) residues was conducted by reaction with dimethyl sulfonate at 22° C. for 10 min. Cleavage at adenine (A) residues was conducted by 12 min reaction at 90° C. in 1.5M NaOH 1mM EDTA. Cleavage at cytosine (C) residues was conducted using hydrazine in 2M NaCl for 13 min at 22° C. Cleavage at thymine (T) residues was conducted using hydrazine with no added NaCl for 10 min at 22° C. Following cleavage, all reactions were twice precipitated using ethanol and thoroughly dried. All samples were reacted with 1M piperidine at 90° C. for 30 min. Piperidine was removed by evaporation in a Savant speed vac concentrator. Fragments were separated by electrophoresis in acrylamide gels (BRL HO apparatus) in 8M urea, 50 mM Tris-borate (pH 8.3), 1 mM EDTA. Detection of degraded ladder was by autoradiography using Kodak XAR5 film at –70° C.

Cloning of λMAC117

High molecular weight DNA (6 μg) from tumor λMAC117 (see above) was digested with 12 units restriction enzyme Eco RI (New England Biolabs) in a volume of 100 μl for about one hour at 37° C. DNA was obtained by phenol $CHCl_3$ extraction and ethanol precipitation and resuspended in water at a concentration of 0.1 μg/ml. This DNA (0.2 μg) was ligated to λwes λB arms (Bethesda Research Labs) (1 μg) using T4 DNA ligase (New England Biolabs) in a total volume of 20 ml [50 mM Tris-HCl pH 7.4, 10 mM $MgCl_2$ 10 mM dithiothreitol, 0.5 mM spermidine, 1 mM ATP]. This mixture of ligated DNAs was packaged into infectious bacteriophage particles using the Packagene system (Promega Biotec). These particles were used to infect bacteria BNN45 and about $8\times10^5$ individual phage plaques were obtained.

These phage plates were screened for individual plaques containing DNA homologous to the v-erbB probes (described above) using standard procedures. Briefly, bacterial culture plates containing approximately 15,000 plaques were grown overnight. Sterile nitrocellulose discs (Schleicher and Schuell) were applied to the dish, removed and allowed to air dry for about 90 minutes. The discs were then treated with 0.2M NaOH, 1.5M NaCl followed by 0.4M Tris-HCl pH 7.5 followed by 0.3M NaCl 0.03M Na citrate and baked in vacuo for two hours at 80° C. These discs were then exposed to hybridization and washing conditions identical to those described for FIG. 2 using the identical v-erbB probe. Washing conditions were also identical to those for FIG. 2. Hybridization was detected by autoradiography at –70° C. for 16 hours. Single hybridizing phage plaques were obtained by three successive hybridization experiments (as described above) to isolate a pure phage culture.

DNA from MAC117 was digested with Eco RI, then ligated into bacteriophage λgtWES, packaged in vitro and transferred to Escherichia coli (E. coli) strain BNN45 by infection following standard techniques well known in the art. A library of $4\times10^5$ bacteriophages was screened by plaque hybridization with radioactive v-erbB DNA. Ten of 14 hybridizing phages contained a 6-kbp Eco RI fragment. FIG. 1 shows the physical map of one of these phages, λMAC117, and pMAC117, a pUC12 subdlone containing a 2-kbp Bam HI fragment of λMAC117 that hybridized with v-erbb probes. The region of pMAC 117 to which v-erbB hybridized most intensely was flanked by Acc I and Nco I sites. Human repetitive sequences were also localized (FIG. 1, region demarcated by arrows).

A deposit of pMAC117 cloned in E. coli has been made at the American Type Culture Collection (ATCC), Bethesda, Mass. under accession number 53408. Upon issuance of a patent, the culture will continue to be maintained for at least 30 years and made available to the public without restriction subject, of course, to the provisions of the law in this respect.

Figure 2A:
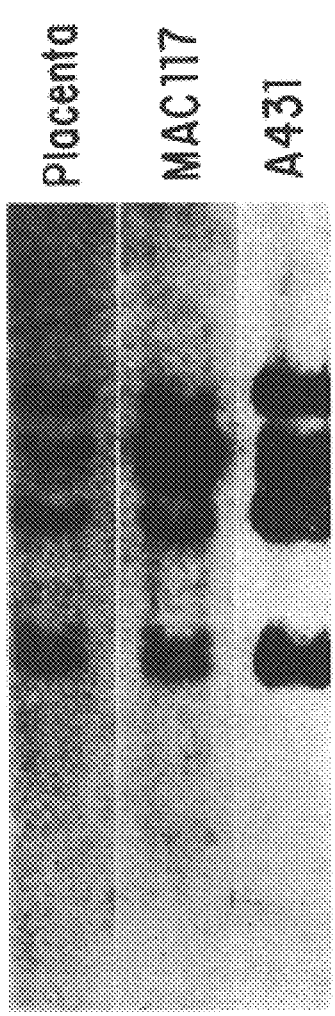
FIG. 2, parts A and B, shows the gel electrophoretic properties of specific gene fragments: detection of v-erbB- and pMAC117-specific gene fragments in normal human placenta, A431 cells or human mammary carcinoma MAC117. DNA (15 μg) was cleaved with Eco RI, separated by electrophoresis in agarose gels and transferred to nitrocellulose paper (Southern, *J. Mol. Biol.* 98:503, 1975). Hybridization to the $^{32}$P-labeled probe (Rigby et al., *J. Mol. Biol.* 113:237, 1977) was conducted in a solution of 40 percent formamide, 0.75M NaCl and 0.075M sodium citrate at 42° C. (Wahl et al., *Proc. Natl. Acad. Sci.*, USA 76:3683, 1979). The v-erbB probe (A) was a mixture of the 0.5-kbp Bam HI-Bam HI fragment and the 0.5-kbp Bam HI-Eco RI fragment of avian erythroblastosis proviral DNA. The pMAC117 probe (B) was a 1-kbp Bgl I-Bam HI fragment. After hybridization, the blots were washed first in 0.3M NaCl plus 0.03M sodium citrate at room temperature and then in 0.015M NaCl, 0.0015M sodium citrate and 0.1 percent sodium dodecyl sulfate at 42° C. (v-erbB probed blots) or at 52° C. (pMAC117 probed blots). Hybridization was detected by autoradiography.

As shown in FIG. 2A, DNA prepared from tissue of a human mammary carcinoma, MAC117, showed a pattern of hybridization that differed both from that observed with DNA of normal human placenta and from that observed with the A431 squamous-cell carcinoma line, which contains amplified epidermal growth factor (EGF) receptor genes. In A431 DNA, four Eco RI fragments were detected that had increased signal intensities compared to those of corresponding fragments in placenta DNA (FIG. 2A). In contrast, MAC117DNA contained a single 6-kilobase pair (kbp) fragment, which appeared to be amplified compared to corresponding fragments observed in both A431 and placenta DNAs (FIG. 2A). These findings indicate that the MAC117tumor contained an amplified DNA sequence related to, but distinct from, the cellular erbB proto-oncogene.

Figure 2B:
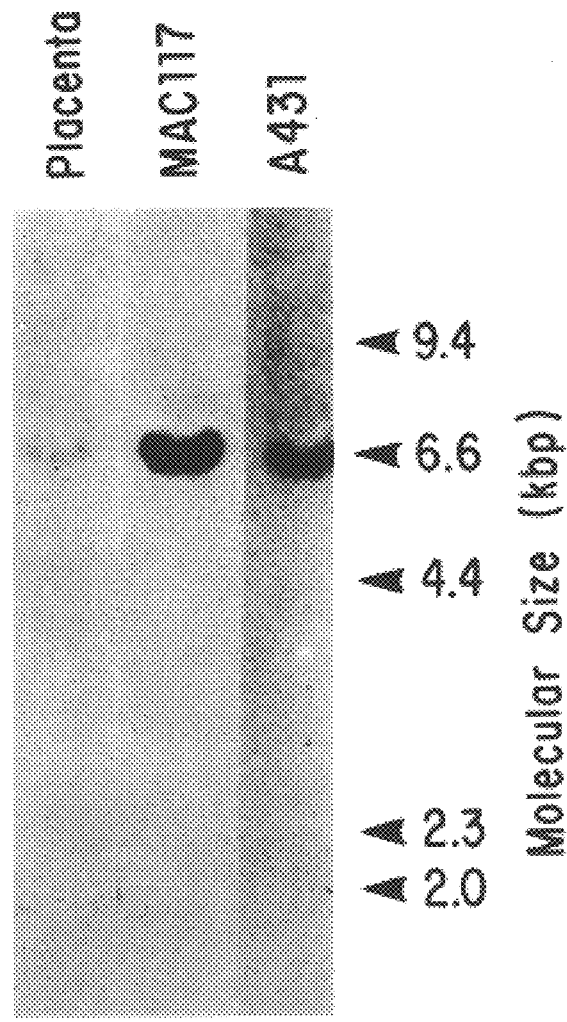

By digestion of pMAC117with Bgl I and Bam HI, it was possible to generate a single-copy probe homologous to v-erbB. This probe detected a 6-kb Eco RI fragment that was amplified in MAC117 DNA and apparently increased in A431 cellular DNA relative to normal DNA (FIG. 2B). The sizes of the fragment corresponded to the amplified 6-kb Eco RI fragment detected in MAC117DNA by means of v-erbB (FIG. 2A). Hybridization to Southern blots containing serial dilutions of MAC117 genomic DNA indicated an approximate amplification of 5- to 10-fold when compared to human placenta DNA.

The nucleotide sequence (SEQ ID NO:2) of the portion of pMAC117 located between the Nco I and Acc I sites contained two regions of nucleotide sequence homologous to v-erbB separated by 122 nucleotides (FIG. 1). These regions shared 69 percent nucleotide sequence identity with both the v-erbB and the human EGF receptor gene. The predicted amino acid sequence of these regions was 85 percent homologous to two regions that are contiguous in the EGF receptor sequence. Furthermore, these two putative coding regions of the MAC117 sequence were each flanked by the AG and GT dinucleotides that border the exons of eukaryotic genes. These findings suggest that the sequence shown in FIG. 1 represents two exons, separated by an intron of a gene related to the erbB/EGF receptor gene.

Figure 3:
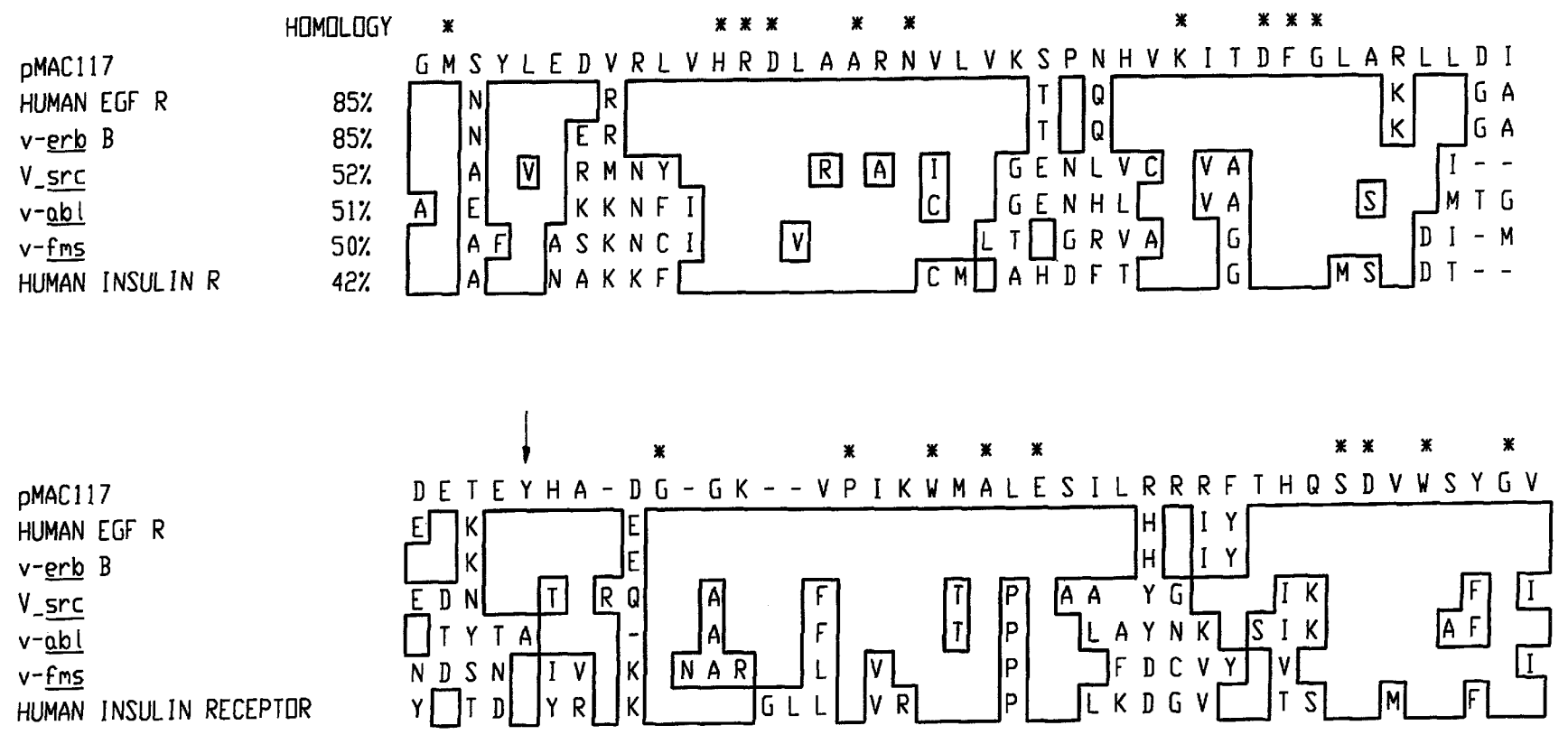

The predicted amino acid sequence SEQ ID NO:1 of the λMAC117 putative exons is homologous to the corresponding sequences of several members of the tyrosine kinase family. The most striking homology was observed with the human EGF receptor or erbB (FIG. 3). In addition, 42 percent to 52 percent homology with the predicted amino acid sequences of other tyrosine kinase-encoding genes was observed. At 25 percent of the positions there was identity among all the sequences analyzed (FIG. 3). A tyrosine residue in the λMAC117 putative coding sequence, conserved among the tyrosine kinases analyzed, is the site of autophosphorylation of the src protein (Smart et al., *Proc. Natl. Acad Sci.* USA, 78:6013, 1981).

Figure 4:
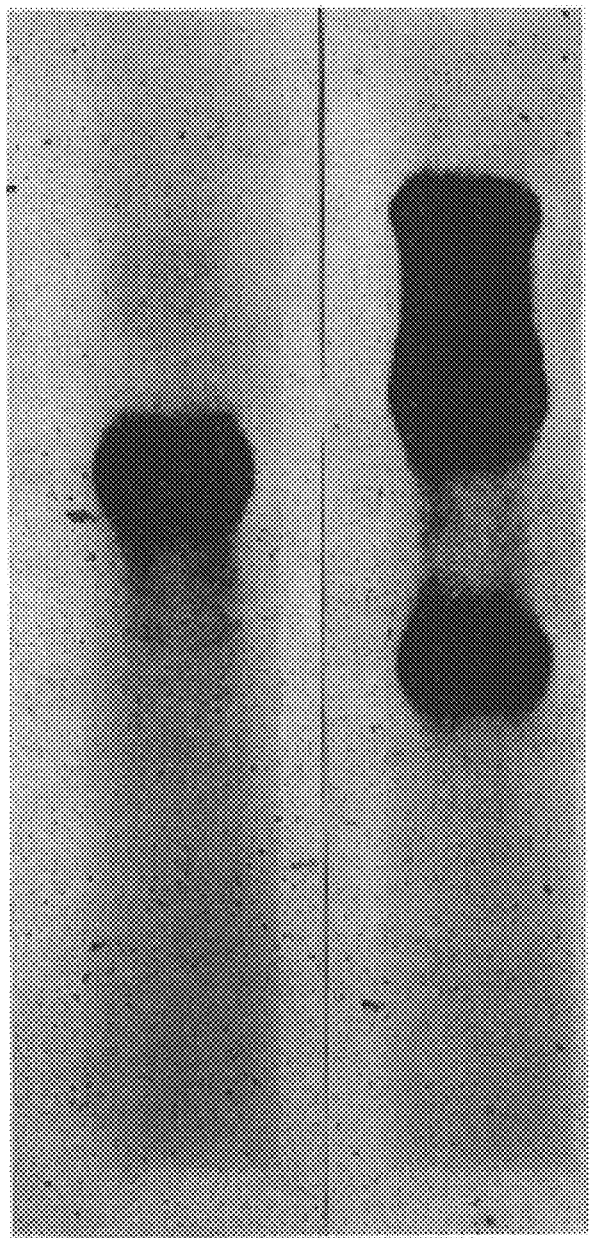
FIG. 4 shows the distinction between λMAC117 and human EGF receptor genes by the detection of distinct messenger RNA species derived from the λMAC117 gene and the human EGF receptor gene. Polyadenylated messenger RNA of A431 cells was separated by denaturing gel electrophoresis in formaldehyde (Lehrach et al., *Biochemistry* 16:4743, 1977), transferred to nitrocellulose (Southern, *J Mol. Biol.* 98:503, 1975), and hybridized under stringent conditions (50 percent formamide, 0.75M NaCl, 0.075M sodium citrate, at 42° C.) with $^{32}$P-labeled probe from pMAC117 (Bgl I-Bam HI fragment) or human EGF receptor complementary DNA (pE7: 2-kb Cla I inserted fragment). Filters were washed under conditions of high stringency (0.015M NaCl plus 0.0015M sodium citrate at 55° C.). Hybridization was detected by autoradiography with exposure times of 4 hours for the pMAC117 probe and 1 hour for the human EGF receptor probe.

The availability of cloned probes of the MAC117 gene made it possible to investigate its expression in a variety of cell types. The MAC117 probe, consisting of the Bgl I to Bam HI restriction fragment of pMAC 117, detected a single 5-kb transcript in A431 cells (FIG. 4). Under the stringent conditions of hybridization utilized, this probe did not detect any of the three RNA species recognized by EGF receptor complementary DNA. Thus, MAC117 represents a new functional gene within the tyrosine kinase family, closely related to, but distinct from the gene encoding the EGF receptor.

There is precedent for the identification of genes related to known oncogenes on the basis of their amplification in human tumors. For example, the high degree of amplification of N-myc in certain malignancies made it detectable by means of the myc gene as a molecular probe (Schwab, *Nature* 305:245, 1983; Kohl et al., *Cell* 35:349, 1983). In the present study, a five-to tenfold amplification of a v-erbB-related gene in the MAC117 mammary carcinoma made it possible to identify this sequence against a complex pattern of EFG receptor gene fragments.

The MAC117 coding sequence, as determined by nucleotide and predicted amino acid sequence, is most closely related to the erbB/EGF receptor among known members of the tyrosine kinase family. The two genes are distinct, however, as evidenced by the sequence diversity and transcript size. Detailed structural analysis of the complete coding sequence would further elucidate the role and function of this v-erb-related gene.

To this purpose we have isolated cDNAs with a complexity of over 4.5 kb from the MAC117 mRNA (Kraus et al., *EMBO Journal* 6:605–610, 1987). A restriction map is shown in FIG. 5A. An oligo (dT) primed normal human fibroblast cDNA library (Okayama and Berg, 1983) was screened with a 0.8 kbp Acc I DNA fragment from the 3' terminus of a genomic clone of MAC117 (FIG. 1). The largest plasmid obtained, pMAC137, carried a 2-kbp insert comprising 1.5 kbp of 3' coding information and 3' untranslated sequence. The remaining coding information upstream was obtained from three phage clones, λMAC30, λMAC10' and λMAC14-1, identified in a randomly primed MCF-7 cDNA library (Walter et al., 1985; FIG. 5A).

Figure 6A:
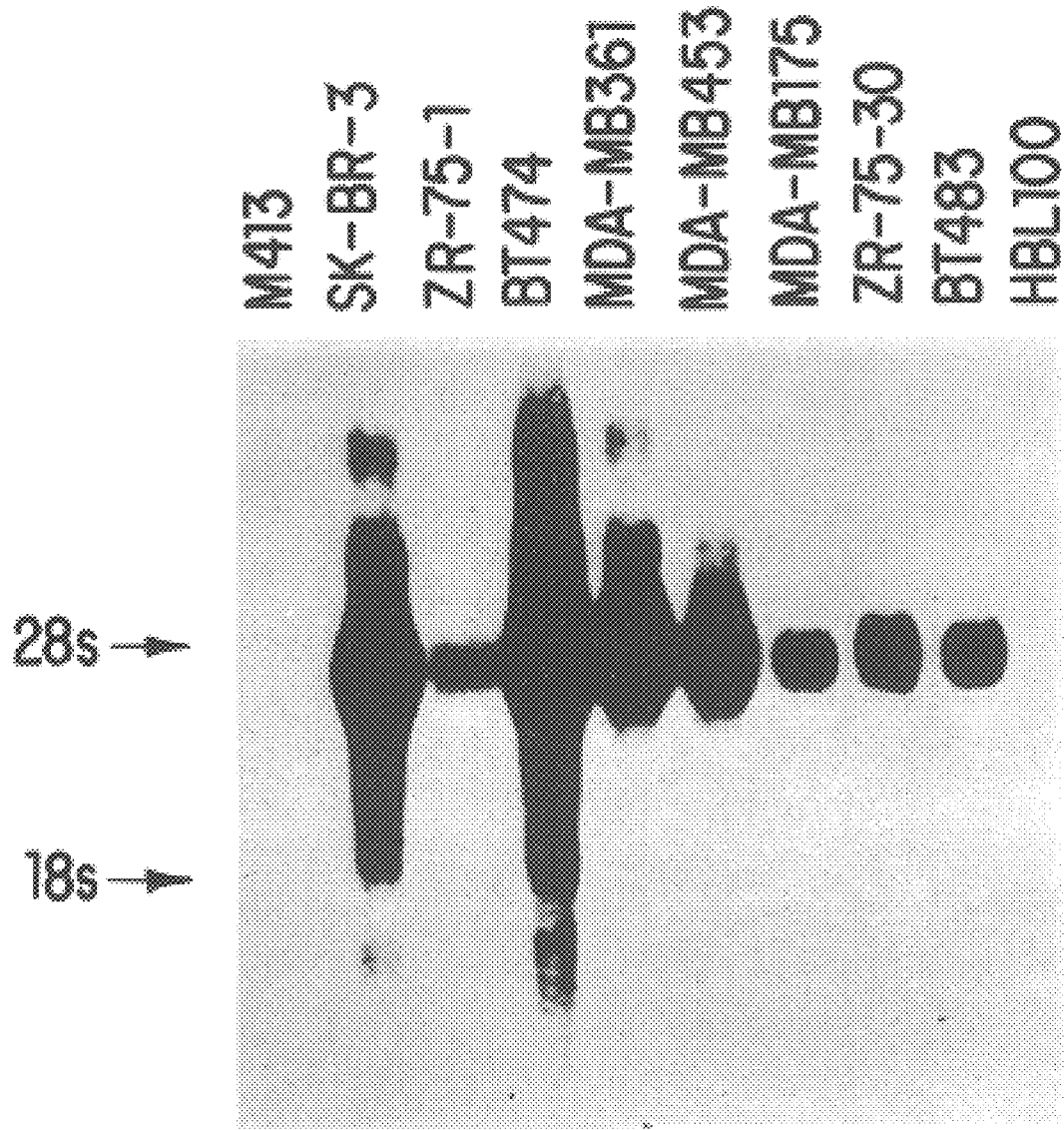
FIG. 6, parts A and B, shows the overexpression of MAC117 in RNA in human mammary tumor cell lines. (A) Northern blot analysis. Total cellular RNA (10 μg) of mammary tumor cell lines, normal fibroblasts M413 and HBL100 was hybridized with a cDNA probe derived from the 5' end of the coding region (FIG. 5B, probe a). M413 and HBL100 cells contain specific MnRNA detectable after longer autoradiographic exposures. Similar results were obtained when probe b or c (FIG. 5B) was employed for hybridization. (B) Quantitation of mRNA levels. Serial 2-fold dilutions of total RNA were applied to nitrocellulose. Replicate filters were hybridized with either a cDNA probe (FIG. 5B, probe b) or human β-actin which served as control for RNA amounts present on the nitrocellulose filter. Relative amounts detected with each probe are indicated in comparison to the hybridization signals observed in normal human fibroblast M413.
Figure 6B:
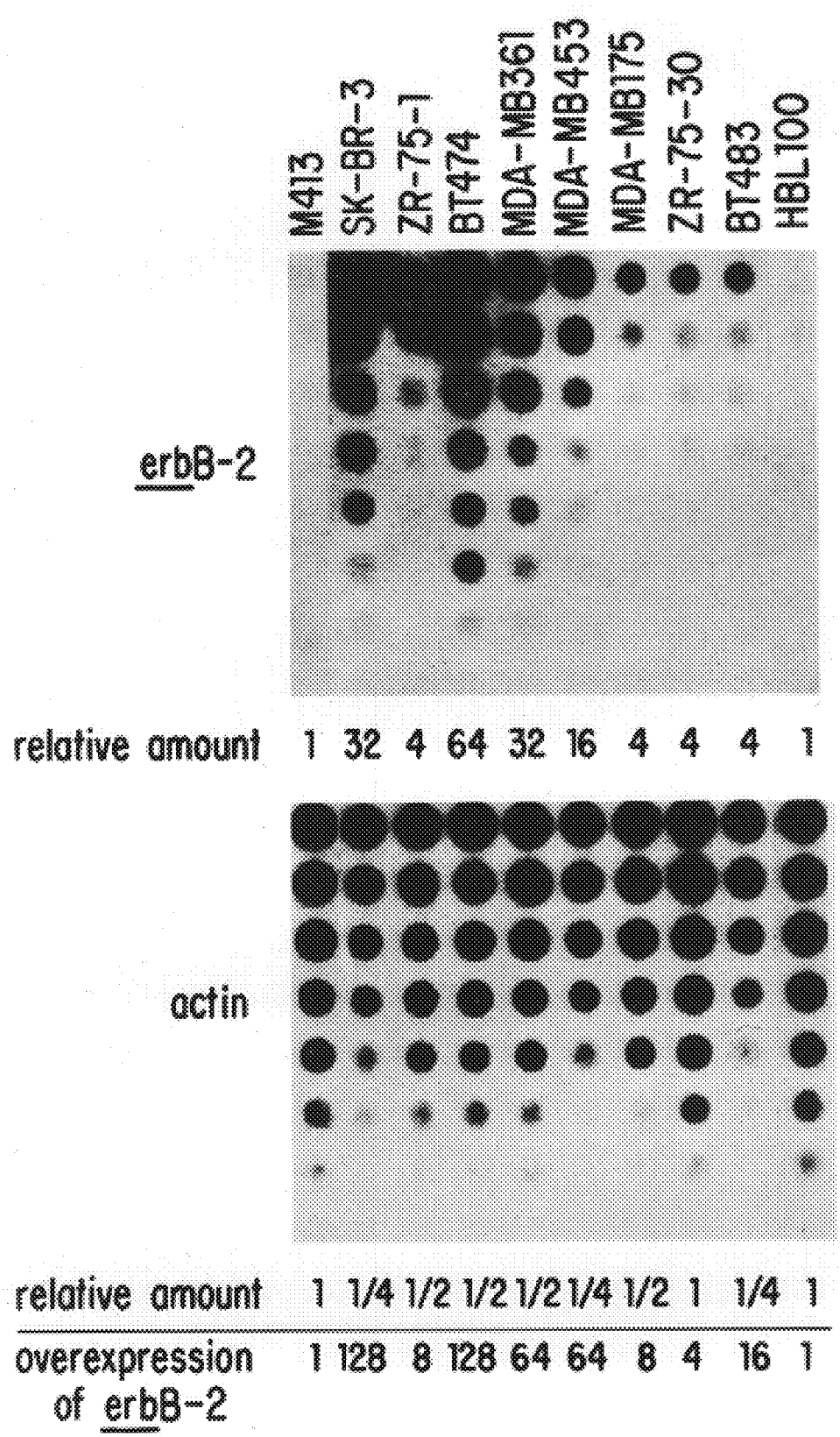

To assess the role of MAC117 in human mammary neoplasia, we compared mRNAs of 16 mammary tumor cell lines to normal human fibroblasts, M413, and a human mammary epithelial cell line, HBL100. Increased expression of an apparently normal size 5-kb transcript was detected in 8 of 16 tumor cell lines when total cellular mRNA was subjected to Northern blot analysis. An aberrantly sized erbB-2 rnRNA was not detected in any of the cell lines analyzed (Kraus et al., *EMBO Journal* 6:605–610, 1987). To quantitate more precisely the amount of MAC117 transcript in eight mammary tumor cell lines which overexpress MAC117, serial 2-fold dilutions of total cellular RNA were subjected to dot blot analysis using human β actin as a control for the amount of RNA applied to the nitrocellulose filters. The highest levels of MAC117 mRNA, which ranged from 64- to 128-fold over that of our controls, were observed in the cell lines MDA-MB453, SK-BR-3, MDA-MB361, and BT474. Moreover, MAC117 mRNA levels were increased 4- to 8-fold in four cell lines including BT483, MDA-MB175, ZR-75-30, and ZR-75-1 (FIG. 6).

Figure 7A:
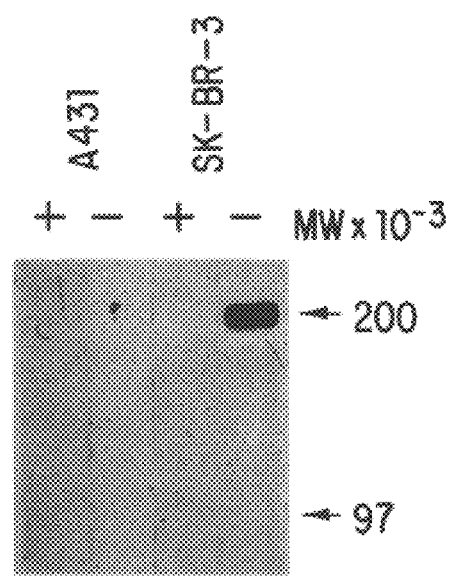
FIG. 7, parts A and B, shows the 185-kDa protein specific for MAC117 and its overexpression in human mammary tumor cell lines. 40 μg total cellular protein was separated by electrophoresis and transferred to nitrocellulose filters. The protein was detected with an antipeptide antibody coupled to $^{125}$I protein A. The specificity of antibody detection was determined by pre-incubation of the antibody with excess amounts of peptide prior to immunodetection. (+) preincubation with peptide, (−) no peptide. In panel B, nonspecific bands at 100 kDa are observed in longer exposures of peptide blocked immunoblots (panel A).
Figure 7B:
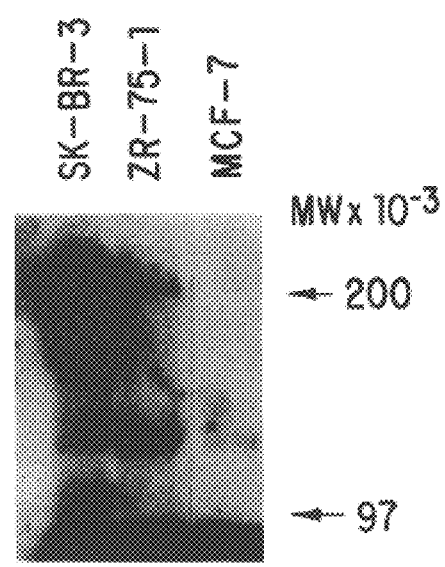

To determine if the overexpression of MAC117 mRNA resulted in a steady state increase of its encoded gene product, we developed a specific immunoblot assay. Antisera were raised against a synthetic peptide whose sequence corresponded to a portion of the putative tyrosine kinase domain of MAC117. As this region is partially conserved between the encoded proteins of the EGFR and MAC117 genes, we tested its specificity using A431 and SK-BR-3 cell lines which overexpress EGFR or MAC117 mRNA, respectively. As shown in FIG. 7A, a specific band of ~185 kd was detected in extracts of SK-BR-3 but not in A431 cells. This band was not detected when the antibody was preincubated with the synthetic peptide corresponding to its antigen. To estimate the relative amounts of MAC117 protein in different mammary tumor cell lines, imnmunoblot analysis was conducted using equivalent amounts of total cellular protein. As shown in FIG. 7B, an intense band of protein was detected in extracts of SK-BR-3 and a less intense but readily detectable band in extracts of ZR-75-1. No MAC117 protein was detected in extracts of MCF-7, a mammary tumor cell line, that did not display overexpression of erbB-2 mRNA. We interpret these results to indicate that substantially more erbB-2 protein is found in both SK-BR-3 and ZR-75-1 than in MCF-7 cells where the amount of protein escapes the sensitivity of the assay. These observations indicated that elevated mRNA levels of MAC117 are translated into MAC117 proteins. This demonstrated that gene amplification of MAC117 results in overexpression of rnRNA and protein of MAC117 in human mammary tumor cells. Furthermore, increased mRNA and protein levels are observed in mammary tumor cells in the absence of gene amplification suggestive for an additional mechanism as a result of which mRNA and protein of our novel v-erbB-related gene can be found overexpressed in tumor cells (Kraus et al., 1987).

Figure 9:
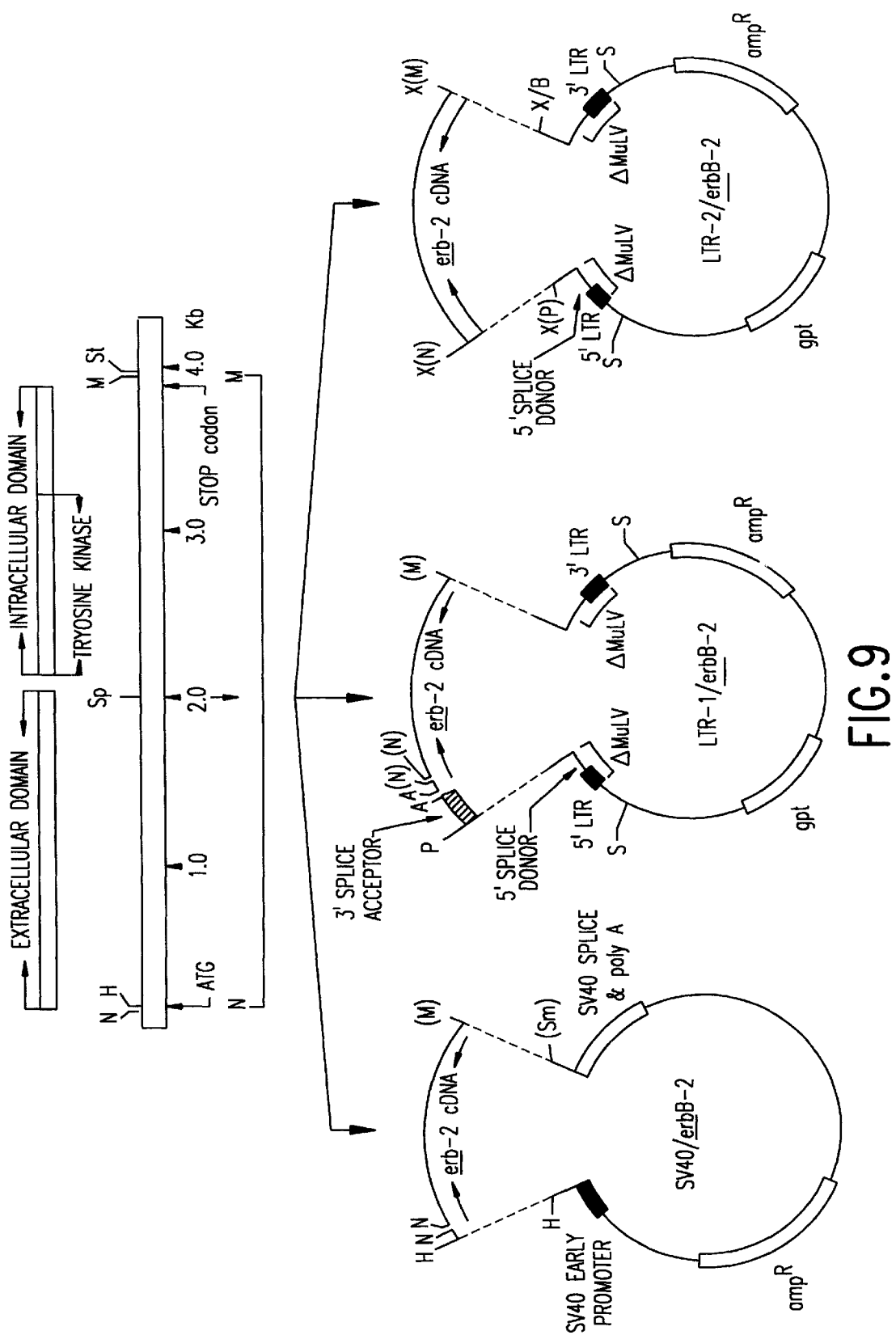
FIG. 9 depicts the construction of expression vectors for the human MAC117 cDNA. A Nco I-Mst II fragment encompassing the entire open reading frame was cloned under the transcriptional control of either the SV40 early promoter or MuLV LTR. Symbols: ▓, erbA-erbB intergenic region of pAEV11 containing the 3' splice acceptor site; N=Nco I, Sp=Sph I, M=Mst II, St=Stu I, H=Hind III, Sm=Sma I, P=Pst I, B=BamH I, X=Xho I. Sites indicated in parenthesis were not reconstituted after the cloning procedures.

To directly assess the effects of MAC117 overexpression on cell growth properties, we assembled a full length normal human MAC117 clone from overlapping cDNA clones (FIGS. 5A,B) linked to the transcription initiation sequences of either the Moloney murine leukemia virus long terminal repeat (MuLV LTR) or the SV40 early promoter in expression vectors in order to express a normal coding sequence of MAC117 in NIH3T3 cells (FIG. 9) (DiFiore et al., *Science* 237:178–182, 1987). Previous studies have indicated different strengths of LTR and the SV40 promoters in these cells (Gorman et al., *Proc. Natl. Acad Sci.* USA, 79:6777, 1982). Because of the presence of the MuLV donor splice site close to the 5' LTR (Shinnick et al., *Nature* 293:543, 1981), we engineered one of the LTR-based vectors (LTR-1/MAC117) to contain an acceptor splice site immediately upstream of the translation initiation codon of the MAC117 coding sequence (FIG. 9). This vector was constructed in order to ensure correct splicing of the message even if a cryptic splice acceptor site were present within the MAC117open reading frame. In the SV40-based expression vector (SV40/MAC117) the erbB-2 coding sequence replaced the neomycin-resistance gene of pSV2/neo (Southern et al., *J. Mol. Appl. Genet.* 1:327, 1982) (FIG. 9). To assess the biologic activity of our human MAC117 vectors, we transfected NIH/3T3 cells with serial dilutions of each DNA. As shown in Table 1, LTR-1/MAC117 DNAs induced transformed foci at high efficiency of $4.1 \times 10^4$ focus-forming units per picomole of DNA (ffu/pM). In striking contrasts, the SV40/erbB-2 construct failed to induce any detectable morphological alteration of NIW3T3 cells transfected under identical assay conditions (Table 1). Since the SV40/erbB-2 construct lacked transforming activity, these results demonstrated that the higher levels of MAC117 expression under LTR influence correlated with its ability to exert transforming activity. To compare the growth properties of NIH/3T3 cells transfected by these genes, we analyzed the transfectants for anchorage-independent growth in culture, a property of many transformed cells. The colony-forming efficiency of a LTR-1/MAC117transformant was very high and comparable to that of cells transformed by LTR-driven v-H-ras and v-erbB (Table 1). Moreover, the LTR-1/MAC117transfectants were as malignant in vivo as cells transformed by the highly potent v-H-ras oncogene and 50-fold more tumorigenic than cells transfected with v-erbB. In contrast, SV40/MAC117 transfectants lacked anchorage-independent growth in vitro and did not grow as tumors in nude mice even when $10^6$ cells were injected (Table 1).

Figure 10:
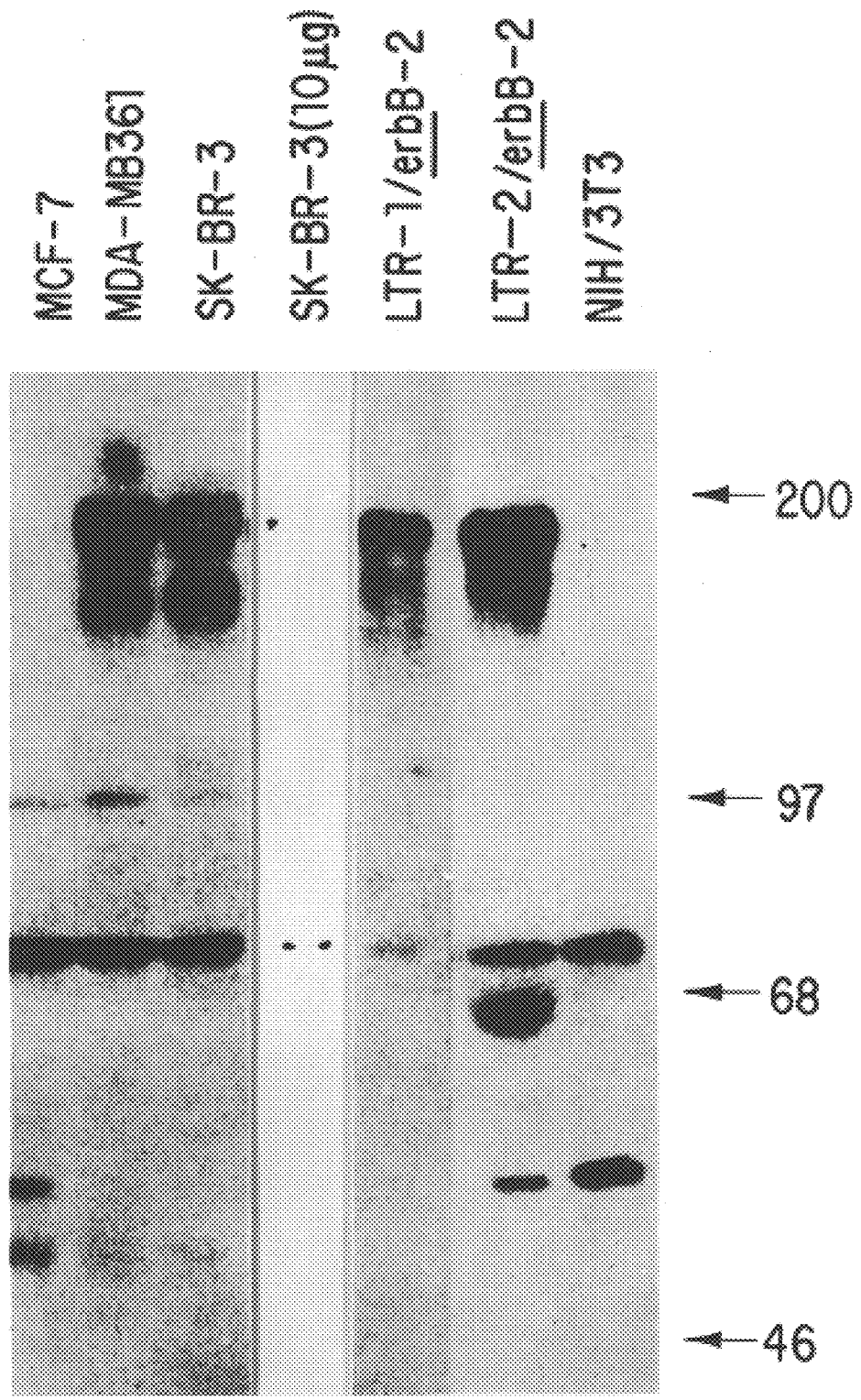
FIG. 10 shows the comparison of the levels of MAC117 proteins in LTR-1/erbB-2 transformed NIH/3T3 cells and human mammary tumor lines by immunoblot analysis. Varying amounts of total cellular protein were separated by electrophoresis and transferred to nitrocellulose filters. The MAC117 protein was detected with rabbit antipeptide serum coupled to $^{125}$I protein A as previously described.

To compare the level of overexpression of the 185-kd protein encoded by MAC117 in human mammary tumor cell lines possessing amplified MAC117 genes with that of NIH/3T3 cells experimentally transformed by the MAC117coding sequence, we compared MAC117 specific protein amounts by Western blotting (DiFiore et al., 1987). An anti-MAC117 peptide serum detected several discrete protein species ranging in size from 150 to 185 kd in extracts of MDA-MB361 and SK-BR-3 mammary tumor cell lines, as well as LTR/MAC117 NIH/3T3 transformants (FIG. 10). The relative levels of the 185-kd MAC117 product were similar in each of the cell lines and markedly elevated over that expressed by MCF-7 cells, where the 185-kd protein was not detectable under these assay conditions (FIG. 10). Thus, human mammary tumor cells which overexpressed the MAC117 gene demonstrated levels of the MAC117 gene product capable of inducing malignant transformation in a model system.

Overexpression of proto-oncogenes can cause cell transformation in culture and may finction in the development of human tumors. Amplification of a normal ras gene or its increased expression under the control of a retroviral long terminal repeat (LTR) induces transformation of NIH 3T3 cells (Chang et al., *Nature* 297:479, 1982). Expression of the normal human sis/PDGF-2 coding sequence in NIH 3T3 cells, which do not normally express their endogenous sis proto-oncogene, also leads to transformation (Gazit et al., *Cell* 39:89,1984; Clarke et al., *Nature* 308:464, 1984). In Burkitt lymphoma, a chromosomal translocation involving myc places its normal coding sequence under the control of an immunoglobulin gene regulatory sequence. The resulting alteration in myc expression is likely to be causally related to tumor development (Nishikura et al., *Science* 224:399, 1984). The observation of amplification of myc or N-myc in more malignant phenotypes of certain tumors has supported the idea that overexpression of these genes can contribute to the progression of such tumors. The erbB/EGF receptor gene is amplified or overexpressed in certain tumors or tumor cell lines. The five- to tenfold amplification of the v-erbB-related gene of the present invention in a mammary carcinoma indicates that increased expression of this gene may have provided a selective advantage to this tumor. The isolation of a new member of the tyrosine kinase gene family amplified in a human mammary carcinoma in accordance with the present invention, makes possible the elucidation of the role of this gene in human malignancy.

Use of Specific Nucleic Acid Probes

As demonstrated in FIGS. 2 and 4, the isolation and use of a Bgl I to Bam HI restriction fragment of pMAC117 to specifically detect the gene and its mRNA product has been set forth. The importance of this technique, involving this probe and others like it, is that the biological functions of the gene described here can be determined and these functions related to practical application, some of which are listed below.

1. Isolation of cloned cDNA. This involves the use of probes specific for the gene described herein; an example is the Bgl I-Bam HI fragment of pMAC117. These probes are made radioactive by standard techniques, such as those noted above, and screening of the libraries of cDNA clones is done using standard methods analogous to those described in "Cloning of λMAC117" above. This approach was employed to clone cDNA comprising the entire coding region of this gene, the restriction map of which is shown in FIG. 5A.

Figure 8A:
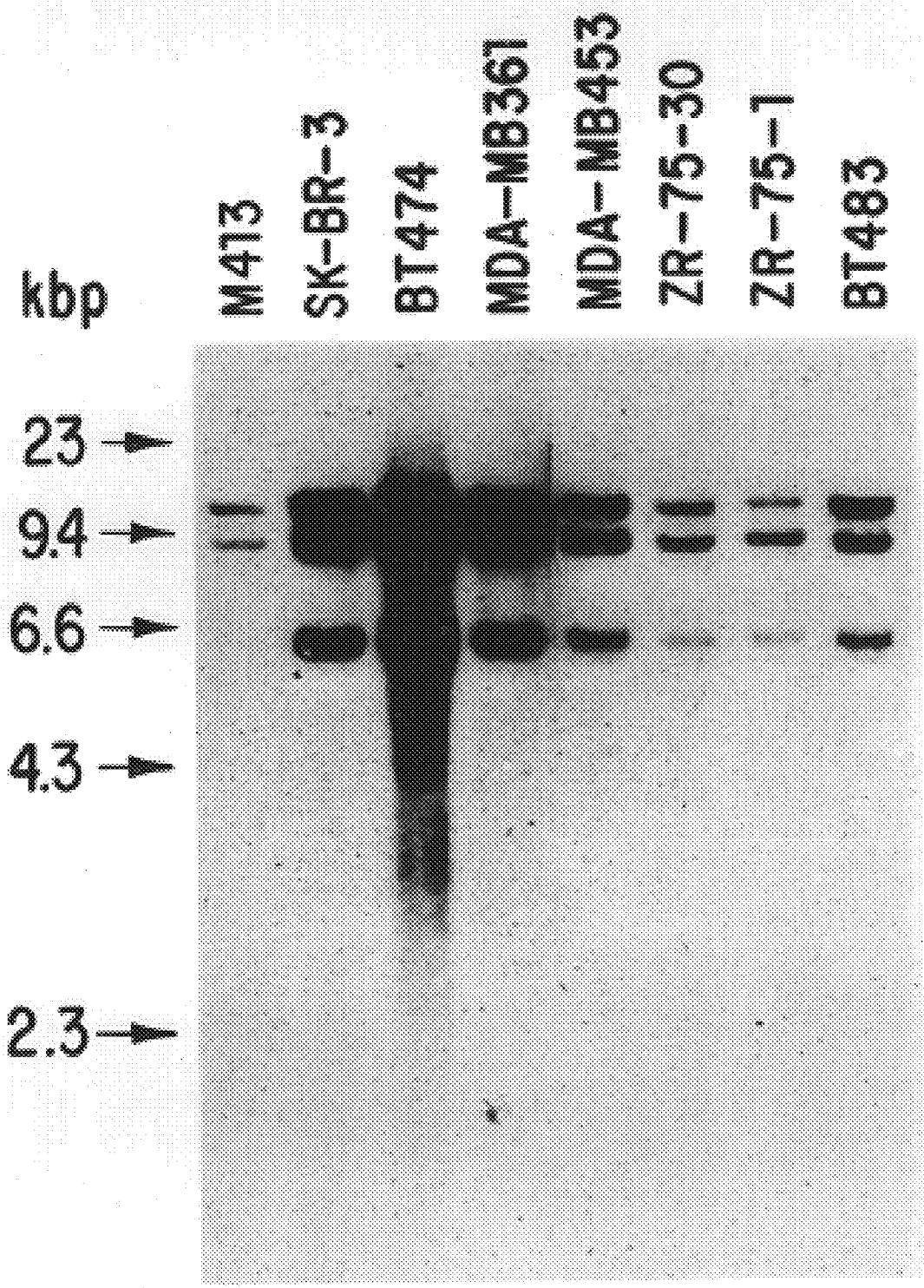
FIG. 8, parts A and B, shows the gene amplification of MAC117 in 4 mammary tumor cell lines and the absence of MAC117 gene amplification in 4 other mammary tumor cell lines overexpressing MAC117 mRNA. (A) Southern blot analysis. For each line 10 μg genomic DNA were restricted with Xba I and hybridized with a probe comprising the entire coding region of MAC117 (FIG. 5B, probe c). Hind III restriction fragments of lambda DNA served as mol. wt. standards. (B) DNA dot-blot analysis. Genomic DNA (10 μg) digested with Eco RI was applied in serial 2-fold dilutions to nitrocellulose filters. Filters were hybridized either with a probe specific for MAC117 (FIG. 5B, probe b) or mos, which served as a control for DNA amounts applied to replace nitrocellulose filters. Gene copy numbers of MAC117 relative to M413 indicate the minimal extent of gene amplification detected in DNA from mammary tumor cell lines.
Figure 8B:
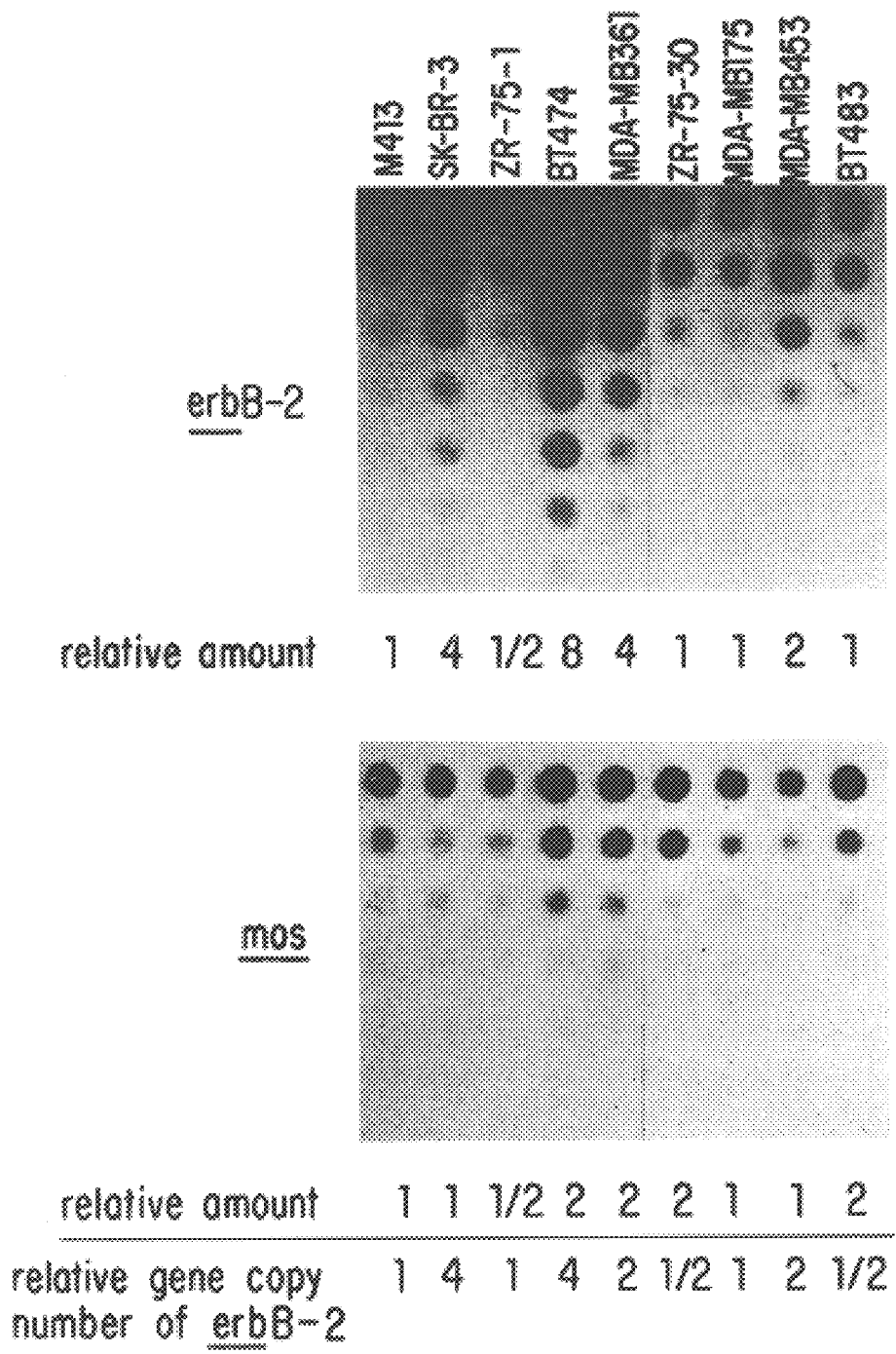

2. Use of cDNA clones. Due to the fact that cDNA clones contain complete information for encoding the protein, these cDNA clones provide a "second generation" of specific probes for the gene described herein. Such probes are shown in FIG. 5B. Their application for hybridization analysis is demonstrated in FIG. 6 and FIG. 8. As shown in FIG. 8, the availability of probes, such as probe c in FIG. 5B, facilitates the comprehensive hybridization analysis of the entire coding region of this gene or any defined part of it. In addition, the complete coding information allows the expression of the protein product in a heterologous system. Such systems utilize strong and/or regulated transcription promoters placed in such a way as to direct overexpression of the gene. Techniques for accomplishing expression of the gene are well known in the art and can be found in such publications as Rosenberg et al., *Methods in Enzym.* 101:123, 1983; Guarante, L., *Methods in Enzym.* 101: 181, 1983. The coding region of our novel v-erbB-related gene was overexpressed under the transcriptional control of MuLV-LTR or SV40 early promoter. Thereby, high expression levels were achieved with MuLV-LTR which caused the neoplastic transformation of transfected cells. These cells can be used as a source to rescue infectious recombinant virus which might prove useful to infect heterologous cells not susceptible to DNA transfection. In addition, these cells serve as a source for high and defined levels of antigen for this novel v-erbB-related gene.

3. Preparation of antibodies specific for the protein product of the gene. Of course, the identification and knowledge of the gene allows its product, protein, for example, to be detected. Poly- or monoclonal antibodies are prepared against said protein by standard techniques, often by commercially available services. The critical reagent in the production of antibodies is the antigen (protein) used. In this case, the antigens are either the peptides chemically synthesized by standard and commercially available techniques according to the predicted amino acid sequences derived from the nucleic acid sequence of the gene or its corresponding cDNA Another potential antigen is the protein itself encoded by the gene and purified from the heterologous expression systems as described above. The antibodies are then employed by standard immunological techniques for the specific detection or diagnostic purposes. Such antibodies were raised against a peptide representing amino acids 35 through 49 of the peptide sequence: GlyMetSerTyrLeuGluAspValArgLeuValHisArgAspLeuAlaAlaArg AsnValLeuValLysSerProAsnHisValLysIleThrAspPheGlyLeuAlaArgLeuLeuAspIleAspGluThrGluTyrHisAlaAspGlyGlyLysValProIleLysTrpMetAlaLeuGluSerIleLeuArgArgArgPheThrHisGlnSerAspValTrpSerTyrGly SEQ ID NO:1). The specificity of these antibodies in detecting the gene product of this novel v-erbB-related gene is demonstrated in FIG. 7A. As shown in FIG. 7B and FIG. 10, these antibodies can be utilized to detect the overexpression of the protein product of our novel v-erb-B-reacted gene in human mammary tumor cells.

Further Applications of the Gene:

Having the knowledge of the gene allows preparing specific nucleic acid probes to detect the gene described here or its mRNA product. The probes are, of course, derived from the gene, such as the Bgl I-Bam HI fragment of pMAC117 used in FIGS. 2 and 4, or alternatively such probes are derived from other regions of the gene or its corresponding cDNA, as shown in FIG. 5B. The use of nucleic acid probes in the molecular diagnosis of human cancer has been documented (Taub et al., *Proc. Natl. Acad Sci.* USA 79:783, 1983; Schwab et al., *Proc. Natl. Acad Sci.* USA 81:4940, 1984). The finding that the gene described here is amplified in a human mammary carcinoma indicates that alterations occur to this gene in human disease. Thus, detection of the amplification or increased expression of this gene provides a useful diagnostic tool for the detection and treatment of human mammary carcinoma or other malignancies resulting from the v-erbB related gene. Hence, diagnostic kits which contain as their principal component specific nucleic acid probes for this gene or its mRNA transcript are of commercial value. The probe is used in analyses similar in concept to those shown in FIG. 2 and FIG. 4 for the detection of gene amplification, structure or the expression of mRNA.

Specific antibody reagents (as described above) capable of detecting the protein product of the gene described herein are employed in a way similar to the use of specific nucleic acid probes. In other words, the expression of aberrant forms and amounts of a gene product is a measure of the related neoplastic condition (Nishikura et al., *Science* 224:399, 1984; Srivastava et al., *Proc. Natl. Acad Sci.* USA 82:38-42, 1985). The detection of the aberrant expression of the protein product of the gene is of importance in the diagnosis of human cancers. As shown in FIG. 7 and FIG. 10, antibodies generated against peptides derived from parts of the amino acid sequence:

GlyMetSerTyrLeuGluAspValArgLeuValHisArgAspLeuAlaAlaARgAsnValLeuValLysSerProAsnHisValLysIleThrAsp-PheGlyLeuAlaArgLeuLeuAspIleAspGluThrGluTyrHisAla AspGlyGlyLysValProIleLysTrp-MetAlaLeuGluSerIleLeuArgArgArgPheThrHisGlnSerAspValTrpSerTyrGly SEQ ID NO:1) specifically detect the protein product of the gene having the nucleotide sequence: GTCTACATGGGTGCTTCCCATTCCAGGG- GATGAGCTACCTGGAGGATGTGC GGCTCGTACA- CAGGGACTTGGCCGCTCGGAACGTGCTG- GTCAAGAGTCCCA ACCATGTCAAAATTACAGACT- TCGGGCTGGCTCGGCTGCTGGACATTGACGA GACAGAGTACCATGCAGATGGGGCAAG- GTTAGGTGAAGGACCAAGGAGC AGAGGAG- GCTGGGTGGAGTGGTGTCTAGCCCATGG- GAGAACTCTGAGTGGC CACCTCCCCACAACACACAGTTGGAG- GACTTCCTCTTCTGCCCTCCCAGGTG CCCAT- CAAGTGGATGGCGCTGGAGTCCATTCTC- CGCCGGCGGTTCACCCACC AGAGTGATGTGTGGAGTTATGGTGTGT- GATGGGGGGTGTTGGGAGGGGTGG GTGAGGAGC- CATGG (SEQ ID NO:2) in human tumor cells. Antibody reagent (produced as described above) is, of course, the critical reagent of the diagnostic kits for this purpose. Such antibody reagents are then employed in such standard methodologies as immunoprecipitation, western blot analysis, immunofluorescence analysis and the like well known in the art. The determination of amplification in a human mammary carcinoma of the gene described here indicates that overexpression (or other abnormality) of the protein product of this gene is functionally important, thus diagnostically relevant. This relevance is further substantiated by the observations that gene amplification of this gene is associated with overexpression of this mRNA and protein in human mammary tumor cells and that protein levels observed in human mammary tumor cell lines exhibiting gene amplification of this gene are sufficient to induce neoplastic transformation of NEH/3T3 cells in vitro. Furthermore, a recent report (Slamon et al., *Science* 235:177–181, 1987) correlates gene amplification of this novel erbB-related gene with a reduced disease free survival in breast cancer patients, suggesting the potential usefulness of analysis of this gene or its gene product as a diagnostic parameter in the clinical setting.

A diagnostic test in accordance with the present invention involves, for example, material obtained by surgical biopsy of potential tumor material. Such material is then analyzed by one or more procedures as follows.

1. DNA is isolated from the sample by standard methods (see above). The DNA is then analyzed by established methods, such as Southern blot hybridization using standard techniques similar to those used in the analysis shown in FIG. 2. Gene-specific probes (described above) are made radioactive by standard techniques and used for detecting genetic abnormalities. Such abnormalities include gene amplification, as seen in the MAC117 tumor sample and tumor cell lines in FIG. 8, or gene rearrangement, as detected by aberrantly migrating bands of hybridization.

2. RNA is isolated from the tumor sample by standard methods (see above). This RNA is analyzed by blot hybridization techniques similar to those described in FIG. 4. Gene-specific probes (described above) are made radioactive by standard techniques and used for detecting the mRNA products of the erbB-related gene described here. Such abnormalities include overexpression or abnormal forms of RNA. Overexpression of an apparently normal sized mRNA is shown in 8 human mammary tumor cell lines in FIG. 6. In addition, mRNA amount may also be quantitated by spot hybridization procedures in which serial dilutions of RNA are fixed to a nitrocellulose filter and the MRNA of the v-erb-B-related gene described here detected by hybridization. Such a procedure has been employed in FIG. 6B. The foregoing techniques are standard. This allows detection of MRNA overexpression or alteration of structure.

When antigens or protein (polypeptides) are to be analyzed, the proteins are separated according to molecular size, for example by gel electrophoresis, transferred to nitrocellulose membranes and the protein product of the erbB-related gene described here detected by reaction with specific antibodies, described above. Such a test is able to detect alterations in the quantity of protein as well as abnormal protein forms. With such an approach protein levels of the v-erb-B-reacted gene have been detected in human mammary tumor cell lines (FIG. 7, FIG. 10).

In addition, specific antibodies may be used in the analysis of histological sections. These techniques, which are well known for other antibody specifications, involve the thin sectioning of biopsied material from a potential tumor, followed by reaction with specific antibodies. The antibody-antigen reaction is then made visible by a variety of standard methods including labeling with fluorescently tagged or ferritin tagged second antisera and the like. Such detection systems allow the detection of the localized aberrant display of the protein product of the erbB-related gene described here.

In addition, although the demonstrated genetic abnormality (shown in FIG. 2) of the gene described here occurs in human mammary carcinoma, genetic abnormalities may also be associated with other clinically important syndromes of neoplastic or other origin. Genetic abnormalities have long been known to be involved in thalassemias, for example.

Knowledge of the erbB-related gene described here also makes possible a means of cancer treatment. If it is found that some cancer cells display abnormally high quantities of the gene product on their surface, such tumors can be treated with antibodies specific for the gene product which have been conjugated to a toxic substance, such as radioactive markers, biological modifiers or toxins and the like. Another treatment modality involves a similar assumption of overexpression. In this approach, a specific natural product, even if unidentified but which has high binding affinity for the protein product of the gene described here, is used to target toxins to the tumor cells. This treatment modality is supported by the finding, reported here, of distinct but limited homology of this gene product to the EGF receptor. If a ligand analogous to EGF exists for the erbB-related gene described here, it may serve as such a targeting agent.

Diagnostic kits for the detection of the protein product of the erbB-related gene.

Kits useful for the diagnosis of human cancers having abnormalities of this gene are now disclosed.

a) Kits designed to detect the protein by immunoblotting. These kits preferably comprise containers containing (a) homogenization solution (50 mM Tris-HCl pH 7.5, 1% sodium dodecyl sulfate and 0.1% β-mercaptoethanol) for the extraction of protein sample from biopsied material from putative tumors; (b) reagents for the preparation of immunoblots of the protein samples (pre-poured acrylamide gels containing 7.5% acrylamide, 0.025% bis acrylamide, 0.38M Tris-HCl pH 8.8, and 0.1% sodium dodecyl sulfate; nitrocellulose sheets formed to the gel size; and transfer buffer containing 0.25M Tris-glycine pH 8.8, 30% methanol); specific antibody reagents for the detection of the protein product of the erbB-related gene (antisera directed against the protein product of the erbB-related gene described here and reaction buffer containing 0.1M Tris-HCl pH 7.5, 5.0M EDTA, 0.25% gelatin, 0.1% nonidet P-40); and reagents and instructions for the visualization and interpretation of antibody-antigen interaction (these include radioactive protein A; biotin conjugated second antiserum, or peroxidase conjugated second antiserum). While this kit includes components ordinarily found and well known in the art, the critical component is the gene product-specific antibodies and buffers or media for performing immunological tests. The antibodies are derived or prepared as described above from either the peptide sequence predicted from the nucleotide sequence of the gene or its mRNA or from the protein product itself through standard immunization procedures.

b) Kits designed for the detection of the protein product of the erbB-related gene in tissue sections. Such kits include instructions for preparation of sections; instructions and standard reagents for the preparation of slides for microscopy; $H_2O_2$ for removal of endogenous peroxidase; instructions for incubation with antibodies specific for the protein product of the erbB-related gene described here in a buffer solution preferably containing phosphate buffered saline; and second antibodies for detection (these may be coupled to peroxidase, biotin, or ferritin); and instructions for visualization of detection complex. In addition the kits may include: reagents and instructions for the preparation of sections from biopsied putative tumor material; specific antibody reagents for the protein product of the erbB-related gene described here and instructions for its reaction with the tissue section; and reagents and instructions for the detection of the protein-antibody interaction either by immunofluorescence, ferritin conjugated second antibodies or other standard methods well known in the art.

A Method for the Treatment of Human Cancers Which Express High Levels of the Protein Product of the Gene Described Herein.

This method involves administering to the patient one of two types of reagent which preferentially binds cells expressing high levels of the protein product of the erbB-related gene described here. These reagents are either antibodies directed against the protein product or a ligand, which is likely to exist because of the homology of the gene to a growth factor receptor. The ligand is isolated by standard techniques using the intrinsic protein kinase activity of the protein product of the erbB-related gene. Extracts of body fluids and cell culture supernatants are incubated with the protein and $\gamma$-$^{32}$P ATP. The presence of ligand is inferred by incorporation of $^{32}$P into the protein. The ligand is then purified by standard techniques such as ion exchange chromatography, gel permeation chromatography, isoelectric focusing, gel electrophoresis and the like. The natural ligand or antibody is tagged with one or more agents which will cause injury to cells to which they bind. Such tagging systems include incorporation of radioactive or biological toxins. The present discovery of amplification of the erbB-related gene makes it likely that some tumors carry large amounts of the corresponding protein. Hence, the two type-specific agents will bind in larger amounts to the protein present in the body and thus direct the toxic effects of the reagents to these cells.

It is understood that the examples and embodiments described herein are for illustrative purposes only and that various modifications or changes in light thereof will be suggested to persons skilled in the art and are to be included within the spirit and purview of this application and the scope of the appended claims.

Table 1 compares transformation characteristics of NIH/3T3 cells transfected with vectors generating different expression levels of the MAC117 coding sequence.

TABLE 1

| DNA transfectant[a] | Specific transforming activity[b] (ffu/pM) | Colony-forming efficiency in agar (%)[c] | Cell number required for 50% tumor incidence[d] |
|---|---|---|---|
| LTR-1/MAC117 | $4.1 \times 10^4$ | 45 | $10^3$ |
| SV40/MAC117 | $<10^0$ | <0.01 | $>10^6$ |

TABLE 1-continued

| DNA transfectant[a] | Specific transforming activity[b] (ffu/pM) | Colony-forming efficiency in agar (%)[c] | Cell number required for 50% tumor incidence[d] |
|---|---|---|---|
| LTR/erbB | $5.0 \times 10^2$ | 20 | $5 \times 10^4$ |
| LTR/ras | $3.6 \times 10^4$ | 35 | $10^3$ |
| pSV2/gpt | $<10^0$ | <0.01 | $>10^6$ |

[a]All transfectants were isolated from plates which received 1 μg cloned DNA and were selected by their ability to grow in the presence of killer HAT medium (Mulligan et al., *Proc. Natl. Acad. Sci.* USA 78:2072, 1981).
[b]Focus-forming units were adjusted to ffu/pM of cloned DNA added based on the relative molecular weights of the respective plasmids.
[c]Cells were plated at 10-fold serial dilutions in 0.33% soft agar medium containing 10% calf serum. Visible colonies comprising >100 cells were scored at 14 days.
[d]NFR nude mice were inoculated subcutaneously with each cell line. Ten mice were tested at cell concentrations ranging from $10^6$ to $10^3$ cells/mouse. Tumor formation was monitored at least twice weekly for up to 30 days.

We claim:

1. A purified nucleic acid which specifically hybridinzes to at least part of a MAC117 gene or nucleic acid derivative thereof and which does not hybridize to a nucleic acid encoding epidermal growth factor receptor under stringent conditions, wherein said MAC117 gene comprises the following sequence:

GTCTACATGGGTGCTTCCCATTCCAGGG-
GATGAGCTACCTGGAGGATGTGCGGCTCG
TACACAGGGACTTGGCCGCTCGGAACGT-
GCTGGTCAAGAGTCCCAACCATGTCAAA
ATTACAGACTTCGGGCTGGCTCGGCT-
GCTGGACATTGACGAGACAGAGTACCATGC
AGATGGGGGCAAGGTTAGGTGAAGGAC-
CAAGGAGCAGAGGAGGCTGGGTGGAGTG
GTGTCTAGCCCATGGGAGAACTCT-
GAGTGGCCACCTCCCCACAACACACAGTTGGA
GGACTTCCTCTTCTGCCCTCCCAGGTGC-
CCATCAAGTGGATGGCGCTGGAGTCCATT CTC-
CGCCGGCGGTTCACCCACCAGAGTGAT-
GTGTGGAGTTATGGTGTGTGATGGGGG
GTGTTGGGAGGGGTGGGTGAGGAGCCATGG
(SEQ ID NO:2).

2. A test kit for detecting genetic abnormalities comprising a container means having disposed therewithin the nucleic acid according to claim 1.

3. A recombinant nucleic acid comprising the nucleic acid according to claim 1 and a vector.

4. A recombinant nucleic acid which contains a gene or gene fragment comprising the nucleic acid sequence cloned in *E coli* in the ATCC deposition under the accession number 53408.

5. The nucleic acid according to claim 3, wherein said vector is a plasmid.

6. A composition of matter comprising at least one nucleic acid defined by claim 1 in a carrier.

7. The composition of matter according to claim 6, wherein the nucleic acid is labeled.

8. A composition of matter comprising a nucleic acid which is fully complementary to and of the same length as nucleic acid according to claim 1 in a carrier.

9. The composition according to claim 7, wherein the nucleic acid is labeled with a radioactive isotope.

10. The composition according to claim 9, wherein said radioactive isotope is $^{32}$P.

11. A cell that contains the recombinant nucleic acid according to claim 3.

12. A nucleic acid filly complementary to and of the same length as the nucleic acid of claim 1.

13. The nucleic acid of claim 1, wherein said nucleic acid comprises at least 24 contiguous nucleotides of said gene.

14. The nucleic acid of claim 1, wherein said nucleic acid comprises at least 40 contiguous nucleotides of said gene and wherein the nucleic acid is fuilly complementary and of the same length.

15. The purified nucleic acid according to claim 1, wherein the nucleic acid derivative of said gene comprises the messenger RNA transcript of said gene.

16. A purified nucleic acid which specifically hybridizes to at least part of a gene or nucleic acid derivative thereof and which does not hybridize to a nucleic acid encoding epidermal growth factor receptor under stringent conditions, wherein said gene comprises the nucleic acid sequence cloned in *E. coli* and deposited with the ATCC under accession number 53408.

17. A purified MAC117 gene wherein said gene comprises the MAC117 sequence:

GTCTACATGGGTGCTTCCCATTCCAGGG-
GATGAGCTACCTGGAGGATGTGCGGCTCG
TACACAGGGACTTGGCCGCTCGGAACGT-
GCTGGTCAAGAGTCCCAACCATGTCAAA
ATTACAGACTTCGGGCTGGCTCGGCT-
GCTGGACATTGACGAGACAGAGTACCATGC
AGATGGGGGCAAGGTTAGGTGAAGGAC-
CAAGGAGCAGAGGAGGCTGGGTGGAGTG
GTGTCTAGCCCATGGGAGAACTCT-
GAGTGGCCACCTCCCCACAACACACAGTTGGA
GGACTTCCTCTTCTGCCCTCCCAGGTGC-
CCATCAAGTGGATGGCGCTGGAGTCCATT CTC-
CGCCGGCGGTTCACCCACCAGAGTGAT-
GTGTGGAGTTATGGTGTGTGATGGGGG
GTGTTGGGAGGGGTGGGTGAGGAGCCATGG
(SEQ ID NO: 2), or allelic variation thereof.

18. The gene according to claim 17, wherein said gene comprises the MAC117 sequence:

GTCTACATGGGTGCTTCCCATTCCAGGG-
GATGAGCTACCTGGAGGATGTGCGGCTCG
TACACAGGGACTTGGCCGCTCGGAACGT-
GCTGGTCAAGAGTCCCAACCATGTCAAA
ATTACAGACTTCGGGCTGGCTCGGCT-
GCTGGACATTGACGAGACAGAGTACCATGC
AGATGGGGGCAAGGTTAGGTGAAGGAC-
CAAGGAGCAGAGGAGGCTGGGTGGAGTG
GTGTCTAGCCCATGGGAGAACTCT-
GAGTGGCCACCTCCCCACAACACACAGTTGGA
GGACTTCCTCTTCTGCCCTCCCAGGTGC-
CCATCAAGTGGATGGCGCTGGAGTCCATT CTC-
CGCCGGCGGTTCACCCACCAGAGTGAT-
GTGTGGAGTTATGGTGTGTGATGGGGG
GTGTTGGGAGGGGTGGGTGAGGAGCCATGG
(SEQ ID NO: 2).

19. A cDNA that encodes a MAC117 protein.

20. A test kit for detecting genetic abnormalities comprising a container means having disposed therewithin the gene according to claim 17.

21. A recombinant nucleic acid comprising the gene according to claim 17 and a vector.

22. A cell that contains the recombinant nucleic acid according to claim 21.

* * * * *